(12) United States Patent
Oka et al.

(10) Patent No.: US 10,781,288 B2
(45) Date of Patent: Sep. 22, 2020

(54) POLYIMIDE PRECURSOR AND POLYIMIDE

(71) Applicant: Ube Industries, Ltd., Ube-shi (JP)

(72) Inventors: Takuya Oka, Ube (JP); Yukinori Kohama, Ube (JP); Yoshiyuki Watanabe, Ube (JP); Nobuharu Hisano, Ube (JP)

(73) Assignee: Ube Industries, Ltd., Ube-Shi (JP)

( * ) Notice: Subject to any disclaimer, the term of this patent is extended or adjusted under 35 U.S.C. 154(b) by 491 days.

(21) Appl. No.: 14/402,553

(22) PCT Filed: Mar. 15, 2013

(86) PCT No.: PCT/JP2013/057563
§ 371 (c)(1),
(2) Date: Feb. 27, 2015

(87) PCT Pub. No.: WO2013/179727
PCT Pub. Date: Dec. 5, 2013

(65) Prior Publication Data
US 2015/0158980 A1    Jun. 11, 2015

(30) Foreign Application Priority Data

May 28, 2012    (JP) ................. 2012-121417

(51) Int. Cl.
| | | |
|---|---|---|
| *C07D 407/08* | (2006.01) | |
| *C08G 73/10* | (2006.01) | |
| *C09D 179/08* | (2006.01) | |
| *C08G 73/14* | (2006.01) | |
| *C08J 5/18* | (2006.01) | |
| *C08G 73/16* | (2006.01) | |
| *C07C 69/757* | (2006.01) | |
| *C07C 235/82* | (2006.01) | |

(52) U.S. Cl.
CPC ........ *C08G 73/1078* (2013.01); *C07C 69/757* (2013.01); *C07C 235/82* (2013.01); *C07D 407/08* (2013.01); *C08G 73/1046* (2013.01); *C08G 73/14* (2013.01); *C08G 73/16* (2013.01); *C08J 5/18* (2013.01); *C09D 179/08* (2013.01); *C08J 2377/00* (2013.01)

(58) Field of Classification Search
CPC ... C07D 407/06; C07C 69/757; C07C 235/82; C08G 73/1078; C08G 73/1046; C08G 73/14; C08J 5/18
USPC ........................................................ 524/606
See application file for complete search history.

(56) References Cited

U.S. PATENT DOCUMENTS

| | | |
|---|---|---|
| 6,160,081 A | 12/2000 | Tanaka et al. |
| 6,998,455 B1 | 2/2006 | Ohta et al. |
| 2003/0104232 A1 | 6/2003 | Kihara et al. |
| 2003/0144420 A1* | 7/2003 | Tsumura ................ C08G 77/50 525/100 |
| 2009/0068403 A1 | 3/2009 | Yasuda et al. |
| 2009/0068454 A1 | 3/2009 | Murakami et al. |
| 2009/0182114 A1 | 7/2009 | Kusaka et al. |
| 2009/0263640 A1* | 10/2009 | Ding ..................... C08G 73/10 428/220 |
| 2010/0187719 A1 | 7/2010 | Oishi et al. |
| 2010/0283047 A1* | 11/2010 | Facchetti ............... H01B 1/127 257/40 |
| 2011/0177321 A1* | 7/2011 | Carney .................. C09J 163/00 428/323 |
| 2013/0079490 A1 | 3/2013 | Matsumoto et al. |
| 2014/0224318 A1 | 8/2014 | Komatsu et al. |

(Continued)

FOREIGN PATENT DOCUMENTS

| | | |
|---|---|---|
| JP | A-H11-282157 | 10/1999 |
| JP | A-2002-69179 | 3/2002 |
| JP | A-2002-146021 | 5/2002 |

(Continued)

OTHER PUBLICATIONS

Yakushin suru Polyimide no Saishin Doko II—Tayoka suru Shurui-Tokusei—Kakosei to Yoto Kakudai no Jittai—"(Japanese)"Current Trend in Polyimide Advancing Rapidly—Actual Circumstances of Diversified Type, Properties, and Workability, and Broadened Applications—Sumibe Techno Research Kabushiki Kaisha, 2000, p. 102.

(Continued)

*Primary Examiner* — Jane L Stanley
(74) *Attorney, Agent, or Firm* — Knobbe Martens Olson & Bear LLP

(57) ABSTRACT

A polyimide precursor including at least one repeating unit represented by the following chemical formula (1):

Chemical formula (1)

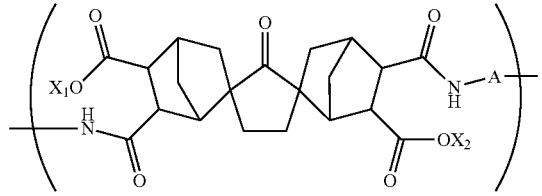

in which A is an arylene group; and $X_1$ and $X_2$ are each independently hydrogen, an alkyl group having 1 to 6 carbon atoms, or an alkylsilyl group having 3 to 9 carbon atoms, and a polyimide obtained from the polyimide precursor has a coefficient of linear thermal expansion from 50° C. to 400° C. of 100 ppm/K or less.

8 Claims, No Drawings

(56) References Cited

U.S. PATENT DOCUMENTS

2016/0137787 A1\* 5/2016 Oka .................. C08G 73/1028
                                                                          524/600
2016/0297995 A1\* 10/2016 Oka .................... C09D 179/08

FOREIGN PATENT DOCUMENTS

| | | |
|---|---|---|
| JP | A-2003-168800 | 6/2003 |
| JP | A-2006-321229 | 11/2006 |
| JP | A-2008-31406 | 2/2008 |
| JP | A-2009-067859 | 4/2009 |
| JP | A-2009-286967 | 12/2009 |
| JP | A-2011-021072 | 2/2011 |
| WO | WO2001/028767 | 4/2001 |
| WO | WO2008/146637 | 12/2008 |
| WO | WO2011/099518 | 8/2011 |
| WO | WO2013/021942 | 2/2013 |

OTHER PUBLICATIONS

International Preliminary Report on Patentability and Written Opinion in corresponding PCT Application No. PCT/JP2013/057563, dated May 14, 2013.
Office Action in Japanese Application No. 2014-518309, dated Feb. 14, 2017.

\* cited by examiner

POLYIMIDE PRECURSOR AND POLYIMIDE

This application is the U.S. National Phase under 35 U.S.C. § 371 of International Application No. PCT/JP2013/057563, filed Mar. 15, 2013, designating the U.S., and published in Japanese as WO 2013/179727 on Dec. 5, 2013, which claims priority to Japanese Patent Application No. 2012-121417, filed May 28, 2012, the entire contents of which are incorporated herein by reference.

TECHNICAL FIELD

The present invention relates to a polyimide having excellent properties such as transparency, bending resistance and high heat resistance, and having a very low coefficient of linear thermal expansion up to a high temperature; and a precursor thereof.

BACKGROUND ART

With the coming of an advanced information society, the developments of optical materials such as an optical fiber and an optical waveguide in the field of optical communications, and optical materials such as a liquid crystal oriented film and a protective film for a color-filter in the field of display devices has recently advanced. In the field of display devices, in particular, a plastic substrate which is light-weight and excellent in flexibility has been studied as an alternative to a glass substrate, and the development of a display which is capable of being bent and rolled has been intensively conducted. Accordingly, there is need for a higher-performance optical material which may be used for such purposes.

Aromatic polyimides are intrinsically yellowish-brown-colored due to the intramolecular conjugation and the formation of charge-transfer complexes. Consequently, as a means of reducing coloring, methods of developing transparency, for example, by introducing fluorine atom into the molecule, imparting flexibility to the main chain, introducing a bulky group as a side chain, or the like to suppress the intramolecular conjugation and the formation of charge-transfer complexes are proposed. In addition, methods of developing transparency by the use of a semi-alicyclic or wholly-alicyclic polyimide which do not form charge-transfer complexes in principle are also proposed.

Patent Literature 1 discloses that a thin-film transistor substrate is obtained by forming a thin-film transistor on a film substrate of a transparent polyimide in which the residue of the tetracarboxylic acid component is an aliphatic group by the use of a conventional film-forming process in order to obtain a thin, light-weight and break-proof active matrix display device. The polyimide concretely used herein is prepared from 1,2,4,5-cyclohexane tetracarboxylic dianhydride as the tetracarboxylic acid component and 4,4'-diaminodiphenyl ether as the diamine component.

Patent Literature 2 discloses a process for producing a colorless transparent resin film formed of a polyimide having excellent colorlessness/transparency, heat resistance and flatness, which is used for a transparent substrate for a liquid crystal display device or an organic EL display device, a thin-film transistor substrate, a flexible wiring substrate, and the like, by a solution-casting method using a particular drying step. The polyimide used herein is prepared from 1,2,4,5-cyclohexane tetracarboxylic dianhydride as the tetracarboxylic acid component and α,α'-bis(4-aminophenyl)-1,4-diisopropylbenzene and 4,4'-bis(4-aminophenoxy)biphenyl as the diamine component, and the like.

Patent Literatures 3 and 4 disclose polyimides which are soluble in organic solvents, and prepared using dicyclohexyl tetracarboxylic acid as the tetracarboxylic acid component and diaminodiphenyl ether, diaminodiphenyl methane, 1,4-bis(4-aminophenoxy)benzene, 1,3-bis(4-aminophenoxy)benzene, 2,2-bis[4-(4-aminophenoxy)phenyl]propane, bis[4-(4-aminophenoxy)phenyl]sulfone, bis[4-(4-aminophenoxy)phenyl]ether or m-phenylenediamine as the diamine component.

Such a semi-alicyclic polyimide, in which an alicyclic tetracarboxylic dianhydride is used as the tetracarboxylic acid component and an aromatic diamine is used as the diamine component, combines transparency, bending resistance and high heat resistance. However, such a semi-alicyclic polyimide generally has a great coefficient of linear thermal expansion of 50 ppm/K or more, and therefore the difference in coefficient of linear thermal expansion between a semi-alicyclic polyimide and a conductive material such as a metal is great, and a trouble such as an increase in warpage may occur during the formation of a circuit board, and there has been a problem of not easily performing a process for forming a fine circuit for use in a display, or the like, in particular.

Patent Literature 5 discloses a polyimide obtained from an alicyclic acid dianhydride containing ester bond and a varied aromatic diamine, and the polyimide of Example 4, for example, has a coefficient of linear thermal expansion at 100° C. to 200° C. of not more than 50 ppm/K. However, the polyimide has a glass-transition temperature of about 300° C., and it is assumed that the film softens and the coefficient of linear thermal expansion becomes much greater at a higher temperature, and there is a risk that a trouble occurs in a process for forming a circuit, which requires low thermal expansibility at a high temperature, as well as at a low temperature.

Patent Literature 6 discloses a polyimide prepared using norbornane-2-spiro-α-cyclopentanone-α'-spiro-2''-norbornane-5,5'',6,6''-tetracarboxylic dianhydride and 4,4'-oxydianiline, and the like. However, no mention is made of transparency, and very low coefficient of linear thermal expansion up to a high temperature.

CITATION LIST

Patent Literature

Patent Literature 1: JP-A-2003-168800
Patent Literature 2: WO 2008/146637
Patent Literature 3: JP-A-2002-69179
Patent Literature 4: JP-A-2002-146021
Patent Literature 5: JP-A-2008-31406
Patent Literature 6: WO 2011/099518

SUMMARY OF INVENTION

Technical Problem

The present invention was made in view of the circumstances as described above, and an object thereof is to improve the coefficient of linear thermal expansion up to a high temperature, as well as at a low temperature, of a semi-alicyclic polyimide in which an alicyclic tetracarboxylic dianhydride is used as the tetracarboxylic acid component and an aromatic diamine is used as the diamine component, and preferably improve the coefficient of linear thermal expansion, while maintaining excellent transparency.

In other words, an object of the present invention is to provide a polyimide having excellent properties such as high transparency, bending resistance and high heat resistance, and having a very low coefficient of linear thermal expansion up to a high temperature; and a precursor thereof.

Solution to Problem

The present invention relates to the following items.

[1] A polyimide precursor comprising at least one repeating unit represented by the following chemical formula (1):

Chemical formula (1)

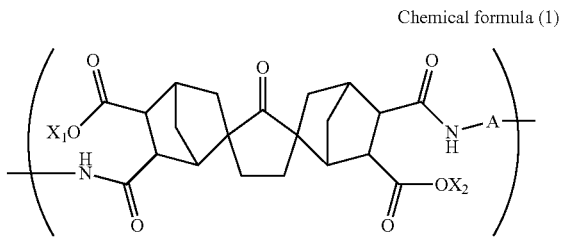

wherein A is an arylene group; and $X_1$ and $X_2$ are each independently hydrogen, an alkyl group having 1 to 6 carbon atoms, or an alkylsilyl group having 3 to 9 carbon atoms, wherein a polyimide obtained from the polyimide precursor has a coefficient of linear thermal expansion from 50° C. to 400° C. of 100 ppm/K or less.

[2] The polyimide precursor as described in [1], wherein a polyimide obtained from the polyimide precursor has a light transmittance at 400 nm of more than 72% in the form of a film having a thickness of 10 μm.

[3] The polyimide precursor as described in [2], wherein a polyimide obtained from the polyimide precursor has a light transmittance at 400 nm of more than 75% in the form of a film having a thickness of 10 μm.

[4] The polyimide precursor as described in any one of [1] to [3], wherein the polyimide precursor comprises at least one repeating unit of the chemical formula (1) in which A is a group represented by the following chemical formula (2):

Chemical formula (2)

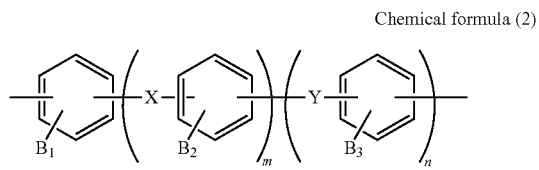

wherein m independently represents 0 to 3; n independently represents 0 to 3; $B_1$, $B_2$ and $B_3$ each independently represent at least one selected from the group consisting of hydrogen atom, methyl group and trifluoromethyl group; and X and Y each independently represent direct bond, or at least one selected from the group consisting of groups represented by the formulas: —NHCO—, —CONH—, —COO— and —OCO—.

[5] The polyimide precursor as described in [4], wherein the polyimide precursor comprises at least two of repeating units of the chemical formula (1) in which A is a group represented by the chemical formula (2).

[6] The polyimide precursor as described in [5], wherein the total content of the repeating units of the chemical formula (1) in which A is a group represented by the chemical formula (2) is 30 mol % or more based on the total repeating units.

[7] The polyimide precursor as described in [5] or [6], wherein the polyimide precursor comprises at least one repeating unit (1-1) of the chemical formula (1) in which A is a structure of the chemical formula (2) in which m and/or n is 1 to 3; and X and/or Y each independently is —NHCO—, —CONH—, —COO— or —OCO—, and at least one repeating unit (1-2) of the chemical formula (1) in which A is a structure of the chemical formula (2) in which m and n are 0, or a structure of the chemical formula (2) in which m and/or n is 1 to 3; and X and Y are direct bond.

[8] The polyimide precursor as described in [7], wherein the polyimide precursor comprises, as the repeating unit (1-1), at least one repeating unit of the chemical formula (1) in which A is a group represented by any one of the following chemical formulas (3-1) to (3-3):

Chemical formula (3-1)

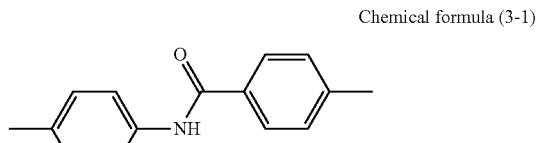

Chemical formula (3-2)

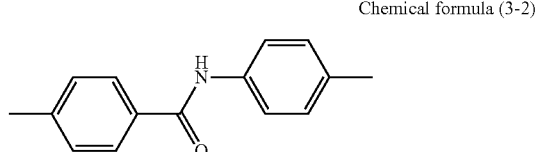

Chemical formula (3-3)

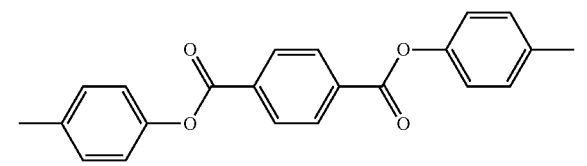

[9] The polyimide precursor as described in [7] or [8], wherein the polyimide precursor comprises, as the repeating unit (1-2), at least one repeating unit of the chemical formula (1) in which A is a group represented by any one of the following chemical formulas (3-4) to (3-6):

Chemical formula (3-4)

Chemical formula (3-5)

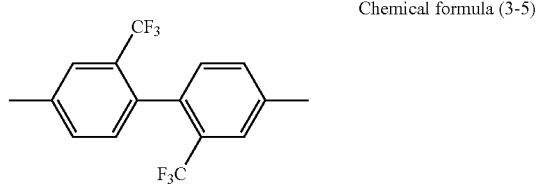

Chemical formula (3-6)

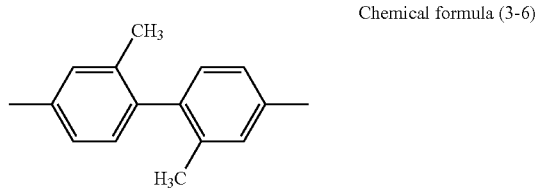

[10] The polyimide precursor as described in any one of [7] to [9], wherein the total content of the repeating unit (1-1) is 30 mol % or more and 70 mol % or less based on the total repeating units, and the total content of the repeating unit (1-2) is 30 mol % or more and 70 mol % or less based on the total repeating units.

[11] The polyimide precursor as described in [4], wherein the polyimide precursor comprises at least one repeating unit of the chemical formula (1) in which A is a group represented by any one of the following chemical formulas (3-1) to (3-6):

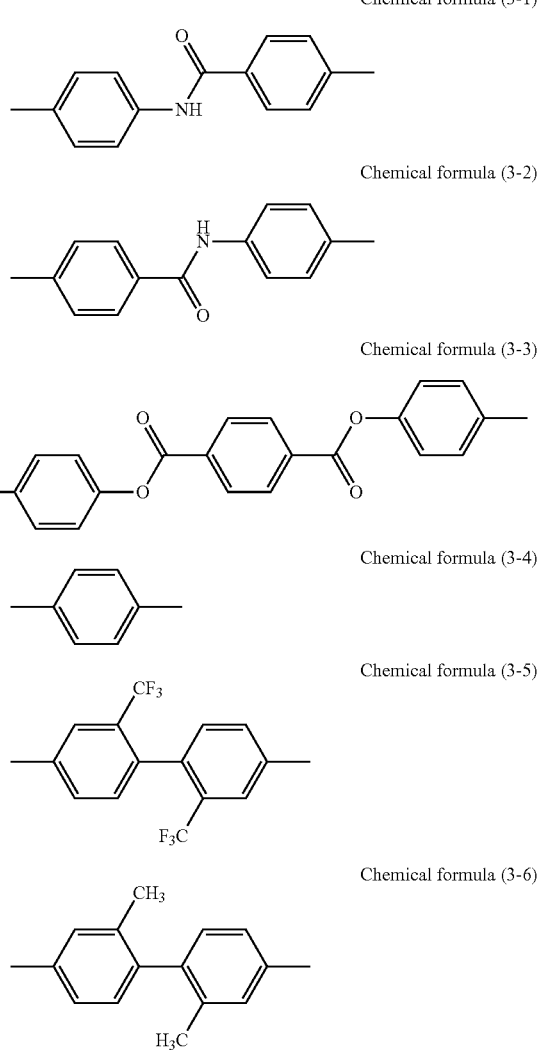

Chemical formula (3-1)

Chemical formula (3-2)

Chemical formula (3-3)

Chemical formula (3-4)

Chemical formula (3-5)

Chemical formula (3-6)

[12] The polyimide precursor as described in [11], wherein the polyimide precursor comprises at least one repeating unit of the chemical formula (1) in which A is a group represented by any one of the chemical formulas (3-1), (3-2), (3-4) and (3-5).

[13] The polyimide precursor as described in [12], wherein the total content of the repeating units of the chemical formula (1) in which A is a group represented by any one of the chemical formulas (3-1), (3-2), (3-4) and (3-5) is 30 mol % or more based on the total repeating units.

[14] A polyimide comprising at least one repeating unit represented by the following chemical formula (5):

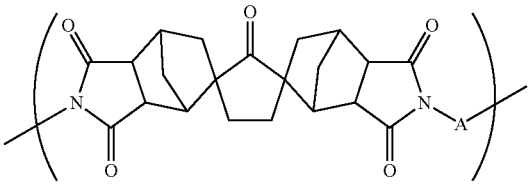

Chemical formula (5)

wherein A is an arylene group,
wherein the polyimide has a coefficient of linear thermal expansion from 50° C. to 400° C. of 100 ppm/K or less.

[15] The polyimide as described in [14], wherein the polyimide has a light transmittance at 400 nm of 72% or more in the form of a film having a thickness of 10 μm.

[16] The polyimide as described in [15], wherein the polyimide has a light transmittance at 400 nm of more than 75% in the form of a film having a thickness of 10 μm.

[17] A polyimide obtained from the polyimide precursor as described in any one of [1] to [13].

[18] A polyimide film obtained from the polyimide precursor as described in any one of [1] to [13].

[19] A varnish comprising the polyimide precursor as described in any one of [1] to [13], or the polyimide as described in any one of [14] to [17].

[20] A polyimide film obtained using a varnish comprising the polyimide precursor as described in any one of [1] to [13], or the polyimide as described in any one of [14] to [17].

[21] A substrate for a display, a touch panel or a solar battery formed of the polyimide obtained from the polyimide precursor as described in any one of [1] to [13], or the polyimide as described in any one of [14] to [17].

Advantageous Effects of Invention

According to the present invention, there may be provided a polyimide having excellent properties such as high transparency, bending resistance and high heat resistance, and having a very low coefficient of linear thermal expansion up to a high temperature; and a precursor thereof. The polyimide obtained from the polyimide precursor of the present invention, and the polyimide of the present invention have high transparency and a low coefficient of linear thermal expansion up to a high temperature, which allows easy formation of a fine circuit, and therefore the polyimides may be suitably used for the formation of a substrate for use in a display, or the like. In addition, the polyimides of the present invention may also be suitably used for the formation of a substrate for a touch panel or a solar battery.

DESCRIPTION OF EMBODIMENTS

The polyimide precursor of the present invention is a polyimide precursor comprising at least one repeating unit represented by the chemical formula (1). The "A" in the chemical formula (1) is an arylene group, preferably an arylene group having 6 to 40 carbon atoms. The chemical formula (1), however, indicates that in two norbornane rings (bicyclo[2.2.1]heptane), the acid group in either 5-position or 6-position reacts with an amino group to form an amide bond (—CONH—) and the other is a group represented by the formula: —COOX$_1$ or a group represented by the formula: —COOX₂, both of which do not form an amide bond. The chemical formula (1) includes all of the four structural isomers, that is, (i) the one having a group represented by the formula: —COOX₁ in the 5-position and a group represented by the formula: —CONH— in the 6-position, and having a group represented by the formula: —COOX₂ in the 5"-position and a group represented by the formula: —CONH-A- in the 6"-position;

(ii) the one having a group represented by the formula: —COOX₁ in the 6-position and a group represented by the formula: —CONH— in the 5-position, and having a group represented by the formula: —COOX₂ in the 5"-position and a group represented by the formula: —CONH-A- in the 6"-position;

(iii) the one having a group represented by the formula: —COOX₁ in the 5-position and a group represented by the formula: —CONH— in the 6-position, and having a group represented by the formula: —COOX₂ in the 6"-position and a group represented by the formula: —CONH-A- in the 5"-position; and (iv) the one having a group represented by the formula: —COOX₁ in the 6-position and a group represented by the formula: —CONH— in the 5-position, and having a group represented by the formula: —COOX₂ in the 6"-position and a group represented by the formula: —CONH-A- in the 5"-position. In other words, the polyimide precursor of the present invention is a polyimide precursor obtained from a tetracarboxylic acid component comprising norbornane-2-spiro-α-cyclopentanone-α'-spiro-2"-norbornane-5,5",6,6"-tetracarboxylic acid, or the like (The term "tetracarboxylic acid, or the like" means tetracarboxylic acid, and tetracarboxylic acid derivatives including tetracarboxylic dianhydride, tetracarboxylic acid silyl ester, tetracarboxylic acid ester and tetracarboxylic acid chloride) and a diamine component comprising an aromatic diamine which has at least one aromatic ring in the chemical structure and preferably has 6 to 40 carbon atoms.

Additionally, the polyimide precursor of the present invention is a polyimide precursor from which a polyimide having a coefficient of linear thermal expansion from 50° C. to 400° C. of 100 ppm/K or less, and preferably having a light transmittance at 400 nm of more than 72%, more preferably more than 75%, in the form of a film having a thickness of 10 μm is obtained.

As the tetracarboxylic acid component, norbornane-2-spiro-α-cyclopentanone-α'-spiro-2"-norbornane-5,5",6,6"-tetracarboxylic acid, or the like may be used alone or in combination of a plurality of types.

The diamine component to be used in the present invention is a diamine component having at least one aromatic ring in the chemical structure, and preferably is a diamine component comprising an aromatic diamine having 6 to 40 carbon atoms.

Examples of the diamine component to be used in the present invention (diamine component to provide a repeating unit of the chemical formula (1)) include, but not limited to, 4,4'-diaminobenzanilide, 3,4'-diaminobenzanilide, 2,2'-bis(trifluoromethyl)benzidine, 9,9-bis(4-aminophenyl)fluorene, 3,3'-diamino-biphenyl, 3,3'-bis(trifluoromethyl)benzidine, 4,4'-oxydianiline, 3,4'-oxydianiline, 3,3'-oxydianiline, p-methylene bis(phenylenediamine), 1,3-bis(4-aminophenoxy)benzene, 1,3-bis(3-aminophenoxy)benzene, 1,4-bis(4-aminophenoxy)benzene, 2,2-bis[4-(4-aminophenoxy)phenyl]hexafluoropropane, 2,2-bis(4-aminophenyl)hexafluoropropane, bis(4-aminophenyl)sulfone, 3,3-bis((aminophenoxy)phenyl)propane, 2,2-bis(3-amino-4-hydroxyphenyl)hexafluoropropane, bis(4-(4-aminophenoxy)diphenyl)sulfone, bis(4-(3-aminophenoxy)diphenyl)sulfone, octafluorobenzidine, 3,3'-dimethoxy-4,4'-diaminobiphenyl, 3,3'-dichloro-4,4'-diaminobiphenyl, 3,3'-difluoro-4,4'-diaminobiphenyl, 4,4'-bis(4-aminophenoxy)biphenyl, 4,4'-bis(3-aminophenoxy)biphenyl, 1,4-diaminocyclohexane, 1,4-diamino-2-methylcyclohexane, 1,4-diamino-2-ethylcyclohexane, 1,4-diamino-2-n-propylcyclohexane, 1,4-diamino-2-isopropylcyclohexane, 1,4-diamino-2-n-butylcyclohexane, 1,4-diamino-2-isobutylcyclohexane, 1,4-diamino-2-sec-butylcyclohexane, 1,4-diamino-2-tert-butylcyclohexane, 1,2-diaminocyclohexane, 1,4-diaminocyclohexane, p-phenylenediamine, m-phenylenediamine, benzidine, m-tolidine, 3,3'-dimethyl-4,4'-diaminobiphenyl, 3,3'-dimethoxy-4,4'-diaminobiphenyl, 3,3'-dichloro-4,4'-diaminobiphenyl, 3,3'-difluoro-4,4'-diaminobiphenyl, 3,3'-diamino-biphenyl, N,N'-bis(4-aminophenyl)terephthalamide, N,N'-p-phenylene bis(p-aminobenzamide), 4-aminophenyl-4-aminobenzoate, bis(4-aminophenyl)terephthalate, biphenyl-4,4'-dicarboxylic acid bis(4-aminophenyl)ester, p-phenylene bis(p-aminobenzoate), bis(4-aminophenyl)-[1,1'-biphenyl]-4,4'-dicarboxylate, [1,1'-biphenyl]-4,4'-diyl bis(4-aminobenzoate), 4,4'-bis(4-aminophenoxy)biphenyl, and 4,4'-bis(3-aminophenoxy)biphenyl, and derivatives thereof. Among them, p-phenylenediamine, m-tolidine, 4,4'-diaminobenzanilide, 4-aminophenyl-4-aminobenzoate, 2,2'-bis(trifluoromethyl)benzidine, and benzidine are preferred, and p-phenylenediamine, m-tolidine, 4,4'-diaminobenzanilide, 4-aminophenyl-4-aminobenzoate, and 2,2'-bis(trifluoromethyl)benzidine are more preferred. Meanwhile, o-tolidine is not preferred because it is highly hazardous.

As the diamine component, the diamine component as described above may be used alone or in combination of a plurality of types.

In the case where a plurality of types of diamines are used in combination, the diamine component preferably comprises at least one of the groups of the following chemical formula (4) in an amount of 30 mol % or more.

Chemical formula (4)

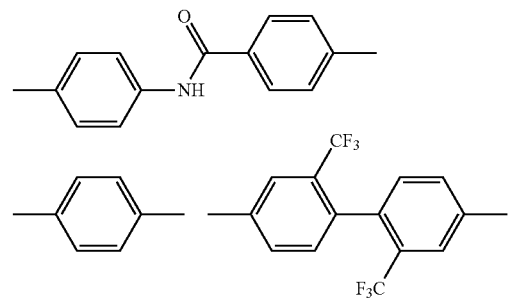

The polyimide precursor of the present invention preferably comprises at least one repeating unit of the chemical formula (1) in which A is a group represented by the chemical formula (2). The diamine component to provide a repeating unit of the chemical formula (1) in which A is a structure of the chemical formula (2) has an aromatic ring, and when the diamine component has a plurality of aromatic rings, the aromatic rings are each independently linked to each other by direct bond, amide bond, or ester bond. When the aromatic rings are linked at the 4-position relative to the amino group or the linking group between the aromatic rings, the obtained polyimide has a linear structure and may have low linear thermal expansibility, although the linking position of the aromatic rings is not limited thereto. Meanwhile, the aromatic ring may be substituted by methyl or trifluoromethyl. The substitution position is not particularly limited.

Examples of the diamine component to provide a repeating unit of the chemical formula (1) in which A is a structure of the chemical formula (2) include, but not limited to, p-phenylenediamine, m-phenylenediamine, benzidine, 3,3'diamino-biphenyl, 2,2'-bis(trifluoromethyl)benzidine, 3,3'-bis(trifluoromethyl)benzidine, m-tolidine, 4,4'-diaminobenzanilide, 3,4'-diaminobenzanilide, N,N'-bis(4-aminophenyl)terephthalamide, N,N'-p-phenylene bis(p-aminobenzamide), 4-aminophenoxy-4-diaminobenzoate, bis(4-aminophenyl)terephthalate, biphenyl-4,4'-dicarboxylic acid bis(4-aminophenyl)ester, p-phenylene bis(p-aminobenzoate), bis(4-aminophenyl)-[1,1'-biphenyl]-4,4'-dicarboxylate, and [1,1'-biphenyl]-4,4'-diyl bis(4-aminobenzoate). The diamine component may be used alone or in combination of a plurality of types. Among them, p-phenylenediamine, m-tolidine, 4,4'-diaminobenzanilide, 4-aminophenoxy-4-diaminobenzoate, 2,2'-bis(trifluoromethyl)benzidine, benzidine, N,N'-bis(4-aminophenyl)terephthalamide, and biphenyl-4,4'-dicarboxylic acid bis(4-aminophenyl)ester are preferred, and p-phenylenediamine, 4,4'-diaminobenzanilide, and 2,2'-bis(trifluoromethyl)benzidine are more preferred. When p-phenylenediamine, 4,4'-diaminobenzanilide, or 2,2'-bis(trifluoromethyl)benzidine is used as the diamine component, the obtained polyimide may combine high heat resistance and high light transmittance. These diamines may be used alone or in combination of a plurality of types. In one embodiment, the one in which the diamine component is only 4,4'-diaminobenzanilide singly may be excluded. In one embodiment, the one in which the diamine component is a combination of 4,4'-diaminobenzanilide and a diamine component which provides a repeating unit of the chemical formula (1) in which A is a structure other than the chemical formula (2) (other diamines other than the diamine component which provides the one in which A is a structure of the chemical formula (2)) may be excluded. Meanwhile, o-tolidine is not preferred because it is highly hazardous.

The polyimide precursor of the present invention preferably comprises at least one repeating unit of the chemical formula (1) in which A is a group represented by the chemical formula (2). In other words, the diamine component to provide a repeating unit of the chemical formula (1) preferably comprises a diamine component to provide a repeating unit of the chemical formula (1) in which A is a structure of the chemical formula (2). When the diamine component to provide the "A" in the chemical formula (1) is a diamine component to provide a structure of the chemical formula (2), the heat resistance of the obtained polyimide may be improved.

In the polyimide precursor of the present invention, the ratio of one or more repeating units of the chemical formula (1) in which A is a structure of the chemical formula (2) is preferably 30 mol % or more, more preferably 50 mol % or more, more preferably 70 mol % or more, more preferably 80 mol % or more, further preferably 90 mol % or more, particularly preferably 100 mol %, in total based on the total repeating units. When the ratio of the repeating unit of the chemical formula (1) in which A is a structure of the chemical formula (2) is less than 30 mol % based on the total repeating units, the coefficient of linear thermal expansion of the obtained polyimide may be greater. In one embodiment, in view of the mechanical properties of the obtained polyimide, the ratio of the diamine component to provide a structure of the chemical formula (2) may be preferably 80 mol % or less, more preferably 90 mol % or less, or less than 90 mol %, in total based on 100 mol % of the diamine component to provide a repeating unit of the chemical formula (1). For example, other diamines such as 4,4'-oxydianiline may be used preferably in an amount of less than 20 mol %, more preferably not more than 10 mol %, more preferably less than 10 mol %, based on 100 mol % of the diamine component to provide a repeating unit of the chemical formula (1).

In the polyimide precursor of the present invention, the "A" is preferably a group represented by any one of the chemical formulas (3-1) to (3-6), more preferably a group represented by any one of the chemical formulas (3-1), (3-2), (3-4) and (3-5).

The total content of the repeating units of the chemical formula (1) in which A is a group represented by any one of the chemical formulas (3-1), (3-2), (3-4) and (3-5) is preferably 30 mol % or more, more preferably 50 mol % or more, more preferably 70 mol % or more, more preferably 80 mol % or more, further preferably 90 mol % or more, particularly preferably 100 mol %, based on the total repeating units.

The polyimide precursor of the present invention preferably comprises at least two types of repeating units of the chemical formula (1) in which A is a group represented by the chemical formula (2). In other words, the diamine component to provide a repeating unit of the chemical formula (1) preferably comprises at least two types of diamine components to provide a repeating unit of the chemical formula (1) in which A is a structure of the chemical formula (2). When the diamine component to provide the "A" in the chemical formula (1) comprises at least two types of diamine components to provide a structure of the chemical formula (2), the balance between high transparency and low linear thermal expansibility of the obtained polyimide may be achieved (that is, a polyimide having high transparency and low coefficient of linear thermal expansion may be obtained).

In the case where the polyimide precursor comprises at least two types of repeating units of the chemical formula (1) in which A is a group represented by the chemical formula (2), the total content of the repeating units of the chemical formula (1) in which A is a group represented by the chemical formula (2) is preferably 30 mol % or more, more preferably 50 mol % or more, more preferably 60 mol % or more, more preferably 70 mol % or more, more preferably 80 mol % or more, further preferably 90 mol % or more, particularly preferably 100 mol %, based on the total repeating units.

The polyimide precursor of the present invention more preferably comprises (i) at least one type of repeating unit (1-1) of the chemical formula (1) in which A is a structure of the chemical formula (2) in which m and/or n is 1 to 3; and X and/or Y each independently is —NHCO—, —CONH—, —COO— or —OCO—, and (ii) at least one type of repeating unit (1-2) of the chemical formula (1) in which A is a structure of the chemical formula (2) in which m and n are 0, or a structure of the chemical formula (2) in which m and/or n is 1 to 3; and X and Y are direct bond.

As the repeating unit (1-1), a repeating unit of the chemical formula (1) in which A is a group represented by any one of the chemical formulas (3-1) to (3-3) is preferred, and a repeating unit of the chemical formula (1) in which A is a group represented by any one of the chemical formulas (3-1) to (3-2) is more preferred. The diamine component to provide a repeating unit of the chemical formula (1) in which A is a group represented by the chemical formula (3-1) or the chemical formula (3-2) is 4,4'-diaminobenzanilide, and the diamine component to provide a repeating unit of the chemical formula (1) in which A is a group represented by the chemical formula (3-3) is bis(4-aminophenyl)terephthalate. These diamines may be used alone or in combination of a plurality of types.

As the repeating unit (1-2), a repeating unit of the chemical formula (1) in which A is a group represented by any one of the chemical formulas (3-4) to (3-6) is preferred, and a repeating unit of the chemical formula (1) in which A is a group represented by any one of the chemical formulas (3-4) to (3-5) is more preferred. The diamine component to provide a repeating unit of the chemical formula (1) in which A is a group represented by the chemical formula (3-4) is p-phenylenediamine, and the diamine component to provide a repeating unit of the chemical formula (1) in which A is a group represented by the chemical formula (3-5) is 2,2'-bis(trifluoromethyl)benzidine, and the diamine component to provide a repeating unit of the chemical formula (1) in which A is a group represented by the chemical formula (3-6) is m-tolidine. These diamines may be used alone or in combination of a plurality of types.

It is preferred that, in the polyimide precursor of the present invention, the ratio of one or more repeating units (1-1) is 30 mol % or more and 70 mol % or less in total based on the total repeating units, and the ratio of one or more repeating units (1-2) is 30 mol % or more and 70 mol % or less in total based on the total repeating units. It is particularly preferred that the ratio of one or more repeating units (1-1) is 40 mol % or more and 60 mol % or less in total based on the total repeating units, and the ratio of one or more repeating units (1-2) is 40 mol % or more and 60 mol % or less in total based on the total repeating units. In one embodiment, the ratio of the repeating unit (1-1) is more preferably less than 60 mol %, more preferably not more than 50 mol %, particularly preferably not more than 40 mol %, in total based on the total repeating units. Additionally, in one embodiment, the polyimide precursor may preferably comprise other repeating units represented by the chemical formula (1) other than the repeating unit (1-1) and the repeating unit (1-2) (for example, the one in which the "A" has a plurality of aromatic rings and the aromatic rings are linked to each other by ether bond (—O—)) preferably in an amount of less than 20 mol %, more preferably not more than 10 mol %, particularly preferably less than 10 mol %, based on the total repeating units.

In the polyimide precursor of the present invention, the diamine component to provide the "A" in the chemical formula (1) (diamine component to provide a repeating unit of the chemical formula (1)) preferably comprises at least two types of diamine components to provide a structure of the chemical formula (2), one of which is 4,4'-diaminobenzanilide. When the diamine component to provide the "A" in the chemical formula (1) comprises at least two types of diamine components to provide a structure of the chemical formula (2), one of which is 4,4'-diaminobenzanilide, a polyimide having high heat resistance in addition to high transparency and low linear thermal expansibility may be obtained.

In the polyimide precursor of the present invention, the diamine component to provide the "A" in the chemical formula (1) (diamine component to provide a repeating unit of the chemical formula (1)) particularly preferably comprises at least one selected from 2,2'-bis(trifluoromethyl)benzidine and p-phenylenediamine, and 4,4'-diaminobenzanilide. When these diamine components are combined together, a polyimide having high transparency and low linear thermal expansibility, and high heat resistance may be obtained.

The diamine component to provide the "A" in the chemical formula (1) (diamine component to provide a repeating unit of the chemical formula (1)) preferably comprises 4,4'-diaminobenzanilide in an amount of 30 mol % or more and 70 mol % or less, and either one or both of p-phenylenediamine and 2,2'-bis(trifluoromethyl)benzidine in an amount of 30 mol % or more and 70 mol % or less, and particularly preferably comprises 4,4'-diaminobenzanilide in an amount of 40 mol % or more and 60 mol % or less, and either one or both of p-phenylenediamine and 2,2'-bis(trifluoromethyl)benzidine in an amount of 40 mol % or more and 60 mol % or less. When the diamine component to provide the "A" in the chemical formula (1) comprises 4,4'-diaminobenzanilide in an amount of 30 mol % or more and 70 mol % or less, and either one or both of p-phenylenediamine and 2,2'-bis(trifluoromethyl)benzidine in an amount of 30 mol % or more and 70 mol % or less, a polyimide having high transparency and low linear thermal expansibility, and high heat resistance may be obtained. In one embodiment, the diamine component to provide the "A" in the chemical formula (1) (diamine component to provide a repeating unit of the chemical formula (1)) more preferably comprises 4,4'-diaminobenzanilide in an amount of less than 60 mol %, more preferably not more than 50 mol %, particularly preferably not more than 40 mol %.

The polyimide precursor of the present invention may be a polyimide precursor obtained using other tetracarboxylic acid components and/or other diamine components. For example, the tetracarboxylic acid component may preferably comprise a tetracarboxylic acid component to provide a repeating unit represented by the chemical formula (1) (that is, norbornane-2-spiro-α-cyclopentanone-α'-spiro-2"-norbornane-5,5",6,6"-tetracarboxylic acid, or the like) in an amount of 70 mol % or more and other tetracarboxylic acid components in an amount of 30 mol % or less based on 100 mol % of the total tetracarboxylic acid components.

In addition, other aromatic or aliphatic tetracarboxylic acid components which are generally used for polyimides may be used together in a small amount (preferably 30 mol % or less, more preferably 10 mol % or less, more preferably less than 10 mol %) to the extent that the characteristic properties of the polyimide of the present invention can be exhibited.

In other words, the polyimide precursor of the present invention may be the one comprising other repeating units other than the repeating unit represented by the chemical formula (1), and the ratio thereof is preferably 30 mol % or less, more preferably 10 mol % or less, more preferably less than 10 mol %, in total based on the total repeating units.

Examples of the other aromatic or aliphatic tetracarboxylic acid component (tetracarboxylic acid component to provide other repeating units) which may be used in the present invention include derivatives of, and dianhydrides of (4arH,8acH)-decahydro-1t,4t:5c,8c-dimethanonaphthalene-2t,3t,6c,7c-tetracarboxylic dianhydride, (4arH,8acH)-decahydro-1t,4t:5c,8c-dimethanonaphthalene-2c,3c,6c,7c-tetracarboxylic dianhydride, cyclohexane-1,2,4,5-tetracarboxylic acid, 1,2,3,4-cyclobutane tetracarboxylic dianhydride, [1,1'-bi(cyclohexane)]-3,3',4,4'-tetracarboxylic acid, [1,1'-bi(cyclohexane)]-2,3,3',4'-tetracarboxylic acid, [1,1'-bi(cyclohexane)]-2,2',3,3'-tetracarboxylic acid, 4,4'- methylene bis(cyclohexane-1,2-dicarboxylic acid), 4,4'-(propane-2,2-diyl)bis(cyclohexane-1,2-dicarboxylic acid), 4,4'-oxybis(cyclohexane-1,2-dicarboxylic acid), 4,4'-thio bis(cyclohexane-1,2-dicarboxylic acid), 4,4'-sulfonyl bis (cyclohexane-1,2-dicarboxylic acid), 4,4'-(dimethylsilanediyl)bis(cyclohexane-1,2-dicarboxylic acid), 4,4'-(tetrafluoropropane-2,2-diyl)bis(cyclohexane-1,2-dicarboxylic acid), octahydropentalene-1,3,4,6-tetracarboxylic acid, bicyclo[2.2.1]heptane-2,3,5,6-tetracarboxylic acid, 6-(carboxymethyl)bicyclo[2.2.1]heptane-2,3,5-tricarboxylic acid, bicyclo[2.2.2]octane-2,3,5,6-tetracarboxylic acid, bicyclo[2.2.2]octa-5-ene-2,3,7,8-tetracarboxylic acid, tricyclo[4.2.2.0 2,5]decane-3,4,7,8-tetracarboxylic acid, tricyclo[4.2.2.0 2,5]deca-7-ene-3,4,9,10-tetracarboxylic acid, 9-oxatricyclo[4.2.1.0 2,5]nonane-3,4,7,8-tetracarboxylic acid, 3,3',4,4'-biphenyl tetracarboxylic dianhydride, pyromellitic dianhydride, 2,3,3',4'-biphenyl tetracarboxylic dianhydride, 3,3',4,4'-benzophenone tetracarboxylic dianhydride, 2,2-bis(3,4-dicarboxyphenyl)hexafluoropropane dianhydride, bis(3,4-dicarboxyphenyl)methane dianhydride, 4,4'-oxydiphthalic anhydride, bis(3,4-dicarboxyphenyl)sulfone dianhydride, m-terphenyl-3,4,3',4'-tetracarboxylic dianhydride, p-terphenyl-3,4,3',4'-tetracarboxylic dianhydride, bis(3,4-dicarboxyphenyl)sulfide dianhydride, p-phenylene bis(trimellitic monoester anhydride), ethylene bis (trimellitic monoester anhydride), bisphenol A bis(trimellitic monoester anhydride), 2,2-bis(3,4-dicarboxyphenyl)-1,1,1,3,3,3-hexafluoropropane dianhydride, 2,2-bis(2,3-dicarboxyphenyl)-1,1,1,3,3,3-hexafluoropropane dianhydride, 1,2,5,6-naphthalene tetracarboxylic dianhydride, 2,3,6,7-naphthalene tetracarboxylic dianhydride, 1,4,5,8-naphthalene tetracarboxylic dianhydride, 2,2-bis{4-[4-(1,2-dicarboxy)phenoxy]phenyl}propane dianhydride, 2,2-bis{4-[3-(1,2-dicarboxy)phenoxy]phenyl}propane dianhydride, bis{4-[4-(1,2-dicarboxy)phenoxy]phenyl}ketone dianhydride, bis{4-[3-(1,2-dicarboxy)phenoxy]phenyl}ketone dianhydride, 4,4'-bis[4-(1,2-dicarboxy)phenoxy]biphenyl dianhydride, 4,4'-bis[3-(1,2-dicarboxy)phenoxy]biphenyl dianhydride, bis{4-[4-(1,2-dicarboxy)phenoxy] phenyl}ketone dianhydride, bis{4-[3-(1,2-dicarboxy)phenoxy]phenyl}ketone dianhydride, bis{4-[4-(1,2-dicarboxy) phenoxy]phenyl}sulfone dianhydride, bis{4-[3-(1,2-dicarboxy)phenoxy]phenyl}sulfone dianhydride, bis{4-[4-(1,2-dicarboxy)phenoxy]phenyl}sulfide dianhydride, and bis{4-[3-(1,2-dicarboxy)phenoxy]phenyl}sulfide dianhydride, and the like. Among them, derivatives and dianhydrides of bicyclo[2.2.1]heptane-2,3,5,6-tetracarboxylic acid, bicyclo[2.2.2]octane-2,3,5,6-tetracarboxylic acid, (4arH,8acH)-decahydro-1t,4t:5c,8c-dimethanonaphthalene-2t,3t,6c,7c-tetracarboxylic dianhydride, and (4arH,8acH)-decahydro-1t,4t:5c,8c-dimethanonaphthalene-2c,3c,6c,7c-tetracarboxylic dianhydride, and the like are more preferred, because the polyimide is easily produced, and the obtained polyimide has excellent heat resistance and transparency. These may be used alone or in combination of a plurality of types.

In the present invention, other aromatic or aliphatic diamines other than the diamine component which provides a repeating unit of the chemical formula (1) in which A is a structure of the chemical formula (2) as described above may be used. Examples of the other diamine component include 4,4'-oxydianiline, 3,4'-oxydianiline, 3,3'-oxydianiline, p-methylene bis(phenylenediamine), 1,3-bis(4-aminophenoxy)benzene, 1,3-bis(3-aminophenoxy)benzene, 1,4-bis(4-aminophenoxy)benzene, 2,2-bis[4-(4-aminophenoxy) phenyl]hexafluoropropane, 2,2-bis(4-aminophenyl) hexafluoropropane, bis(4-aminophenyl)sulfone, 3,3-bis ((aminophenoxy)phenyl)propane, 2,2-bis(3-amino-4-hydroxyphenyl)hexafluoropropane, bis(4-(4-aminophenoxy)diphenyl)sulfone, bis(4-(3-aminophenoxy) diphenyl)sulfone, octafluorobenzidine, 3,3'-dimethoxy-4,4'-diaminobiphenyl, 3,3'-dichloro-4,4'-diaminobiphenyl, 3,3'-difluoro-4,4'-diaminobiphenyl, 9,9-bis(4-aminophenyl) fluorene, 4,4'-bis(4-aminophenoxy)biphenyl, 4,4'-bis(3-aminophenoxy)biphenyl, 1,4-diaminocyclohexane, 1,4-diamino-2-methylcyclohexane, 1,4-diamino-2-ethylcyclohexane, 1,4-diamino-2-n-propylcyclohexane, 1,4-diamino-2-isopropylcyclohexane, 1,4-diamino-2-n-butylcyclohexane, 1,4-diamino-2-isobutylcyclohexane, 1,4-diamino-2-sec-butylcyclohexane, 1,4-diamino-2-tert-butylcyclohexane, 1,2-diaminocyclohexane, and 1,4-diaminocyclohexane, and derivatives thereof. These may be used alone or in combination of a plurality of types.

The purity of the tetracarboxylic acid component to be used in the present invention may be preferably, but not limited to, 99% or more, more preferably 99.5% or more. (In the case where the component contains a plurality of structural isomers, the purity is determined on the condition that the structural isomers are regarded as the same component without distinguishing them. In the case where a plurality of types of tetracarboxylic acid components are used, the purity is the value of the tetracarboxylic acid component having the highest purity, or the average value of the purities of all tetracarboxylic acid components to be used which are determined separately and weighted with the mass ratio of the used components; for example, the purity of the tetracarboxylic acid component used is calculated to be 97% when 70 parts by mass of a tetracarboxylic acid component having a purity of 100% and 30 parts by mass of a tetracarboxylic acid component having a purity of 90% are used). When the purity is less than 98%, the molecular weight of the polyimide precursor may not be sufficiently increased and the obtained polyimide may have low heat resistance. The purity is a value which may be determined by gas chromatography analysis or $^1$H-NMR analysis. In the case of a tetracarboxylic dianhydride, the purity may be determined by subjecting the tetracarboxylic dianhydride to hydrolysis treatment to form a tetracarboxylic acid, and determining the purity of the tetracarboxylic acid.

The purity of the diamine component to be used in the present invention may be preferably, but not limited to, 99% or more, more preferably 99.5% or more. (In the case where a plurality of types of diamine components are used, the purity is the value of the diamine component having the highest purity, or the average value of the purities of all diamine components to be used which are determined separately and weighted with the mass ratio of the used components; for example, the purity of the diamine component used is calculated to be 97% when 70 parts by mass of a diamine component having a purity of 100% and 30 parts by mass of a diamine component having a purity of 90% are used). When the purity is less than 98%, the molecular weight of the polyimide precursor may not be sufficiently increased and the obtained polyimide may have low heat resistance. The purity is a value which may be determined by gas chromatography analysis.

In the polyimide precursor of the present invention, $X_1$ and $X_2$ in the chemical formula (1) are each independently hydrogen, an alkyl group having 1 to 6 carbon atoms, preferably having 1 to 3 carbon atoms, or an alkylsilyl group having 3 to 9 carbon atoms. As for $X_1$ and $X_2$, the types of the functional groups and the introduction ratio of the functional groups may be changed by the production method as described later.

In the case where $X_1$ and $X_2$ are hydrogen, a polyimide tends to be easily produced therefrom.

Meanwhile, in the case where $X_1$ and $X_2$ are each an alkyl group having 1 to 6 carbon atoms, preferably having 1 to 3 carbon atoms, the polyimide precursor tends to have excellent storage stability. In this case, $X_1$ and $X_2$ are more preferably methyl or ethyl.

Additionally, in the case where $X_1$ and $X_2$ are each an alkylsilyl group having 3 to 9 carbon atoms, the polyimide precursor tends to have excellent solubility. In this case, $X_1$ and $X_2$ are more preferably trimethylsilyl or t-butyldimethylsilyl.

When an alkyl group or an alkylsilyl group is introduced, $X_1$ and $X_2$ may be converted into an alkyl group or an alkylsilyl group in a ratio of 25% or more, preferably 50% or more, more preferably 75% or more, although the introduction ratio of the functional groups is not limited thereto.

According to the chemical structure $X_1$ and $X_2$ have, the polyimide precursors of the present invention may be classified into 1) polyamic acid ($X_1$ and $X_2$ are hydrogen), 2) polyamic acid ester (at least part of $X_1$ and $X_2$ is an alkyl group), and 3) 4) polyamic acid silyl ester (at least part of $X_1$ and $X_2$ is an alkylsilyl group). Each class of the polyimide precursors of the present invention may be easily produced by the following production methods. However, the method for producing the polyimide precursor of the present invention is not limited to the following production methods.

1) Polyamic Acid

The polyimide precursor of the present invention may be suitably obtained, in the form of a polyimide precursor solution composition, by reacting a tetracarboxylic dianhydride as a tetracarboxylic acid component and a diamine component in a substantially equimolar amount, preferably in a molar ratio of the diamine component to the tetracarboxylic acid component [molar number of the diamine component/molar number of the tetracarboxylic acid component] of 0.90 to 1.10, more preferably 0.95 to 1.05, in a solvent at a relatively low temperature of 120° C. or less, for example, to suppress the imidization.

More specifically, the polyimide precursor may be obtained by dissolving the diamine in an organic solvent, adding the tetracarboxylic dianhydride to the resulting solution gradually while stirring the solution, and then stirring the solution at a temperature of 0° C. to 120° C., preferably 5° C. to 80° C., for 1 hour to 72 hours, although the method for synthesizing the polyimide precursor of the present invention is not limited thereto. When they are reacted at a temperature of 80° C. or more, the molecular weight may vary depending on the temperature history in the polymerization and the imidization may proceed by heat, and therefore the polyimide precursor may not be stably produced. The sequence of the addition of the diamine and the tetracarboxylic dianhydride in the production method as described above is preferred because the molecular weight of the polyimide precursor is apt to increase. Meanwhile, the sequence of the addition of the diamine and the tetracarboxylic dianhydride in the production method as described above may be reversed, and the sequence is preferred because the amount of the precipitate is reduced.

In addition, when the diamine component is excessive in the molar ratio of the tetracarboxylic acid component to the diamine component, a carboxylic acid derivative may be added in an amount which substantially corresponds to the excessive molar number of the diamine component, as necessary, so that the molar ratio of the tetracarboxylic acid component to the diamine component is closer to the substantially equimolar amount. As the carboxylic acid derivative to be used herein, tetracarboxylic acids, which do not substantially increase the viscosity of the polyimide precursor solution, that is, do not substantially involve the molecular chain extension, or tricarboxylic acids and anhydrides thereof, and dicarboxylic acids and anhydrides thereof, which function as an end-stopping agent, and the like are preferred.

2) Polyamic Acid Ester

A diester dicarboxylic acid chloride may be obtained by reacting a tetracarboxylic dianhydride and an arbitrary alcohol to provide a diester dicarboxylic acid, and then reacting the diester dicarboxylic acid and a chlorinating agent (thionyl chloride, oxalyl chloride, and the like). The polyimide precursor may be obtained by stirring the diester dicarboxylic acid chloride and a diamine at a temperature of −20° C. to 120° C., preferably −5° C. to 80° C., for 1 hour to 72 hours. When they are reacted at a temperature of 80° C. or more, the molecular weight may vary depending on the temperature history in the polymerization and the imidization may proceed by heat, and therefore the polyimide precursor may not be stably produced. In addition, the polyimide precursor may also be easily obtained by dehydrating/condensing a diester dicarboxylic acid and a diamine by the use of a phosphorus-based condensing agent, a carbodiimide condensing agent, or the like.

The polyimide precursor obtained by the method is stable, and therefore the polyimide precursor may be subjected to purification, for example, reprecipitation in which a solvent such as water and alcohols is added thereto.

3) Polyamic Acid Silyl Ester (Indirect Method)

A silylated diamine may be obtained by reacting a diamine and a silylating agent in advance. The silylated diamine may be purified by distillation, or the like, as necessary. And then, the polyimide precursor may be obtained by dissolving the silylated diamine in a dehydrated solvent, adding a tetracarboxylic dianhydride to the resulting solution gradually while stirring the solution, and then stirring the solution at a temperature of 0° C. to 120° C., preferably 5° C. to 80° C., for 1 hour to 72 hours. When they are reacted at a temperature of 80° C. or more, the molecular weight may vary depending on the temperature history in the polymerization and the imidization may proceed by heat, and therefore the polyimide precursor may not be stably produced.

As for the silylating agent to be used herein, the use of a silylating agent containing no chlorine is preferred because it is unnecessary to purify the silylated diamine. Examples of the silylating agent containing no chlorine atom include N,O-bis(trimethylsilyl)trifluoroacetamide, N,O-bis(trimethylsilyl)acetamide, and hexamethyldisilazane. Among them, N,O-bis(trimethylsilyl)acetamide, and hexamethyldisilazane are particularly preferred, because they contain no fluorine atom and are inexpensive.

In addition, in the silylation reaction of diamine, an amine catalyst such as pyridine, piperidine and triethylamine may be used so as to accelerate the reaction. The catalyst may be used, as it is, as a catalyst for the polymerization of the polyimide precursor.

4) Polyamic Acid Silyl Ester (Direct Method)

The polyimide precursor may be obtained by mixing a polyamic acid solution obtained by the method 1) and a silylating agent, and then stirring the resulting mixture at a temperature of 0° C. to 120° C., preferably 5° C. to 80° C., for 1 hour to 72 hours. When they are reacted at a temperature of 80° C. or more, the molecular weight may vary depending on the temperature history in the polymerization and the imidization may proceed by heat, and therefore the polyimide precursor may not be stably produced.

As for the silylating agent to be used herein, the use of a silylating agent containing no chlorine is preferred because it is unnecessary to purify the silylated polyamic acid, or the obtained polyimide. Examples of the silylating agent containing no chlorine atom include N,O-bis(trimethylsilyl)trifluoroacetamide, N,O-bis(trimethylsilyl)acetamide, and hexamethyldisilazane. Among them, N,O-bis(trimethylsilyl)acetamide, and hexamethyldisilazane are particularly preferred, because they contain no fluorine atom and are inexpensive.

All of the production methods as described above may be suitably performed in an organic solvent, and as a consequence a varnish of the polyimide precursor of the present invention may be easily obtained.

As the solvent used in the production of the polyimide precursor, for example, aprotic solvents such as N,N-dimethylformamide, N,N-dimethylacetamide, N-methyl-2-pyrrolidone, 1-ethyl-2-pyrrolidone, 1,1,3,3-tetramethylurea, 1,3-dimethyl-2-imidazolidinone and dimethyl sulfoxide are preferred, and N,N-dimethylacetamide and N-methyl-2-pyrrolidone are particularly preferred. However, any solvent may be used without any trouble on the condition that the starting monomer components and the formed polyimide precursor can be dissolved in the solvent, and the structure of the solvent is not limited thereto. Examples of the solvent preferably employed include amide solvents such as N,N-dimethylformamide, N,N-dimethylacetamide and N-methylpyrrolidone; cyclic ester solvents such as γ-butyrolactone, γ-valerolactone, δ-valerolactone, γ-caprolactone, ε-caprolactone and α-methyl-γ-butyrolactone; carbonate solvents such as ethylene carbonate and propylene carbonate; glycol solvents such as triethylene glycol; phenol solvents such as m-cresol, p-cresol, 3-chlorophenol and 4-chlorophenol; acetophenone, 1,3-dimethyl-2-imidazolidinone, sulfolane, and dimethylsulfoxide. In addition, other common organic solvents, namely, phenol, o-cresol, butyl acetate, ethyl acetate, isobutyl acetate, propyleneglycol methyl acetate, ethyl cellosolve, butyl cellosolve, 2-methyl cellosolve acetate, ethyl cellosolve acetate, butyl cellosolve acetate, tetrahydrofuran, dimethoxyethane, diethoxyethane, dibutyl ether, diethylene glycol dimethyl ether, methyl isobutyl ketone, diisobutyl ketone, cyclopentanone, cyclohexanone, methyl ethyl ketone, acetone, butanol, ethanol, xylene, toluene, chlorobenzene, turpentine, mineral spirits, petroleum naphtha-based solvents, and the like may be used. These solvents may be used in combination of a plurality of types.

In the present invention, although the logarithmic viscosity of the polyimide precursor is not limited thereto, the logarithmic viscosity of the polyimide precursor in a N,N-dimethylacetamide solution at a concentration of 0.5 g/dL at 30° C. may be preferably 0.2 dL/g or more, more preferably 0.5 dL/g or more. When the logarithmic viscosity is 0.2 dL/g or more, the molecular weight of the polyimide precursor is high, and therefore the obtained polyimide may have excellent mechanical strength and heat resistance.

In the present invention, it is preferred that the varnish of the polyimide precursor comprises at least the polyimide precursor of the present invention and a solvent, and the total amount of the tetracarboxylic acid component and the diamine component is 5 mass % or more, preferably 10 mass % or more, more preferably 15 mass % or more, based on the total amount of the solvent, the tetracarboxylic acid component and the diamine component. Additionally, it is generally preferred that the total amount is 60 mass % or less, preferably 50 mass % or less. When the concentration, which is approximate to the concentration of the solid content based on the polyimide precursor, is too low, it may be difficult to control the thickness of the obtained polyimide film in the production of the polyimide film, for example.

As the solvent used for the varnish of the polyimide precursor of the present invention, any solvent may be used without any trouble on the condition that the polyimide precursor can be dissolved in the solvent, and the structure of the solvent is not particularly limited. Examples of the solvent preferably employed include amide solvents such as N,N-dimethylformamide, N,N-dimethylacetamide and N-methyl-2-pyrrolidone; cyclic ester solvents such as γ-butyrolactone, γ-valerolactone, δ-valerolactone, γ-caprolactone, ε-caprolactone and α-methyl-γ-butyrolactone; carbonate solvents such as ethylene carbonate and propylene carbonate; glycol solvents such as triethylene glycol; phenol solvents such as m-cresol, p-cresol, 3-chlorophenol and 4-chlorophenol; acetophenone, 1,3-dimethyl-2-imidazolidinone, sulfolane, and dimethylsulfoxide. In addition, other common organic solvents, namely, phenol, o-cresol, butyl acetate, ethyl acetate, isobutyl acetate, propyleneglycol methyl acetate, ethyl cellosolve, butyl cellosolve, 2-methyl cellosolve acetate, ethyl cellosolve acetate, butyl cellosolve acetate, tetrahydrofuran, dimethoxyethane, diethoxyethane, dibutyl ether, diethylene glycol dimethyl ether, methyl isobutyl ketone, diisobutyl ketone, cyclopentanone, cyclohexanone, methyl ethyl ketone, acetone, butanol, ethanol, xylene, toluene, chlorobenzene, turpentine, mineral spirits, petroleum naphtha-based solvents, and the like may be used. Additionally, these may be used in combination of a plurality of types.

In the present invention, although the viscosity (rotational viscosity) of the varnish of the polyimide precursor is not limited thereto, the rotational viscosity, which is measured with an E-type rotational viscometer at a temperature of 25° C. and at a shearing speed of 20 sec$^{-1}$, may be preferably 0.01 to 1000 Pa·sec, more preferably 0.1 to 100 Pa·sec. In addition, thixotropy may be imparted, as necessary. When the viscosity is within the above-mentioned range, the varnish is easy to handle during the coating or the film formation, and the varnish is less repelled and has excellent leveling property, and therefore a good film may be obtained.

As necessary, a chemical imidizing agent (an acid anhydride such as acetic anhydride, and an amine compound such as pyridine and isoquinoline), an anti-oxidizing agent, a filler, a dye, a pigment, a coupling agent such as a silane coupling agent, a primer, a flame retardant, a defoaming agent, a leveling agent, a rheology control agent (flow-promoting agent), a releasing agent, and the like may be added to the varnish of the polyimide precursor of the present invention.

As necessary, an inorganic particle such as silica may be mixed into the varnish of the polyimide precursor of the present invention. Examples of the mixing method include, but not limited to, a method in which an inorganic particle is dispersed in a polymerization solvent, and then a polyimide precursor is polymerized in the solvent; a method in which a polyimide precursor solution and an inorganic particle are mixed; a method in which a polyimide precursor solution and an inorganic particle dispersion are mixed; and a method in which an inorganic particle is added to and mixed with a polyimide precursor solution. For example, a silica particle or a silica particle dispersion may be added to the varnish of the polyimide precursor of the present invention. As for the silica particle to be added, the particle size is preferably 100 nm or less, more preferably 50 nm or less, particularly preferably 30 nm or less. When the particle size of the silica particle to be added is more than 100 nm, the polyimide may be white-turbid. Additionally, in the case where a silica particle dispersion is added to the varnish, "ORGANOSILICASOL DMAc-ST (primary particle size: 10-15 nm, dispersion solvent: N,N-dimethylacetamide) solid content: 20-21%" made by Nissan Chemical Industries, Ltd., and the like may be used, for example. The amount of the silica to be added to the polyimide precursor is preferably 50 vol % or less, more preferably less than 50 vol %, particularly preferably less than 40 vol %, based on the polyimide obtained after imidizing the polyimide precursor. When the silica content is more than 50 vol % relative to the polyimide, the polyimide may be brittle.

The polyimide of the present invention is characterized in that the polyimide comprises at least one repeating unit represented by the chemical formula (5), and has a coefficient of linear thermal expansion from 50° C. to 400° C. of 100 ppm/K or less, and preferably has a light transmittance at 400 nm of more than 72%, more preferably more than 75%, in the form of a film having a thickness of 10 μm. The polyimide of the present invention may be suitably produced by the dehydration/ring closure reaction (imidization reaction) of the polyimide precursor of the present invention as described above. The imidization method is not particularly limited, and any known thermal imidization or chemical imidization method may be suitably applied. Preferred examples of the form of the obtained polyimide include a film, a laminate of a polyimide film and another substrate, a coating film, a powder, a bead, a molded article, a foamed article, and a varnish.

The chemical formula (5) of the polyimide of the present invention corresponds to the chemical formula (1) of the polyimide precursor of the present invention.

In the present invention, although the logarithmic viscosity of the polyimide is not limited thereto, the logarithmic viscosity of the polyimide in a N,N-dimethylacetamide solution at a concentration of 0.5 g/dL at 30° C. may be preferably 0.2 dL/g or more, more preferably 0.4 dL/g or more, particularly preferably 0.5 dL/g or more. When the logarithmic viscosity is 0.2 dL/g or more, the obtained polyimide may have excellent mechanical strength and heat resistance.

In the present invention, it is preferred that the varnish of the polyimide comprises at least the polyimide of the present invention and a solvent, and the amount of the polyimide is 5 mass % or more, preferably 10 mass % or more, more preferably 15 mass % or more, particularly preferably 20 mass % or more, based on the total amount of the solvent and the polyimide. When the concentration is too low, it may be difficult to control the thickness of the obtained polyimide film in the production of the polyimide film, for example.

As the solvent used for the varnish of the polyimide of the present invention, any solvent may be used without any trouble on the condition that the polyimide can be dissolved in the solvent, and the structure of the solvent is not particularly limited. The solvent used for the varnish of the polyimide precursor of the present invention as described above may be used likewise as the solvent.

In the present invention, although the viscosity (rotational viscosity) of the varnish of the polyimide is not limited thereto, the rotational viscosity, which is measured with an E-type rotational viscometer at a temperature of 25° C. and at a shearing speed of 20 sec$^{-1}$, may be preferably 0.01 to 1000 Pa·sec, more preferably 0.1 to 100 Pa·sec. In addition, thixotropy may be imparted, as necessary. When the viscosity is within the above-mentioned range, the varnish is easy to handle during the coating or the film formation, and the varnish is less repelled and has excellent leveling property, and therefore a good film may be obtained.

As necessary, an anti-oxidizing agent, a filler, a dye, a pigment, a coupling agent such as a silane coupling agent, a primer, a flame retardant, a defoaming agent, a leveling agent, a rheology control agent (flow-promoting agent), a releasing agent, and the like may be added to the varnish of the polyimide of the present invention.

As necessary, an inorganic particle such as silica may be mixed into the polyimide of the present invention (polyimide obtained from the polyimide precursor of the present invention). Examples of the mixing method include, but not limited to, a method in which an inorganic particle is dispersed in a polymerization solvent, and then a polyimide precursor is polymerized in the solvent; a method in which a polyimide precursor solution and an inorganic particle are mixed; a method in which a polyimide precursor solution and an inorganic particle dispersion are mixed; a method in which an inorganic particle is mixed into a polyimide solution; and a method in which an inorganic particle dispersion is mixed into a polyimide solution. A silica-containing polyimide may be obtained by imidizing a polyimide precursor in a silica-dispersed polyimide precursor solution in which silica is dispersed by any one of these methods; or by mixing a polyimide solution with a silica particle or a silica-dispersed solution, and then heating and drying the mixture to remove the solvent therefrom. As for the inorganic particle to be dispersed in the polyimide, a silica particle may be added to the polyimide. As for the silica particle to be added, the particle size is preferably 100 nm or less, more preferably 50 nm or less, particularly preferably 30 nm or less. When the particle size of the silica particle to be added is more than 100 nm, the polyimide may be white-turbid. Additionally, in the case where a silica particle dispersion is used, "ORGANOSILICASOL DMAc-ST (primary particle size: 10-15 nm, dispersion solvent: N,N-dimethylacetamide) solid content: 20-21%" made by Nissan Chemical Industries, Ltd., and the like may be used, for example. The amount of the silica to be added is preferably 50 vol % or less, more preferably less than 50 vol %, particularly preferably less than 40 vol %, based on the polyimide. When the silica content is more than 50 vol % relative to the polyimide, the polyimide may be brittle.

The polyimide of the present invention may have preferably, but not limited to, a coefficient of linear thermal expansion from 50° C. to 400° C. of 100 ppm/K or less, more preferably 50 ppm/K or less, more preferably 40 ppm/K or less, particularly preferably 30 ppm/K or less, when the polyimide is formed into a film, and have a very low coefficient of linear thermal expansion.

The polyimide of the present invention may have preferably, but not limited to, a total light transmittance (average light transmittance at wavelengths of 380 nm to 780 nm) of 80% or more, more preferably 85% or more, more preferably 86% or more, particularly preferably 87% or more, in the form of a film having a thickness of 10 μm, and have excellent optical transparency.

The polyimide of the present invention may have preferably, but not limited to, a light transmittance at 400 nm of 70% or more, more preferably 72% or more, more preferably more than 72%, more preferably 75% or more, more preferably more than 75%, more preferably 76% or more, more preferably 77% or more, particularly preferably 80% or more, when the polyimide is formed into a film having a thickness of 10 μm, and have excellent transparency.

As for a film formed of the polyimide of the present invention, the thickness of the film is preferably about 1 μm to about 250 μm, more preferably about 1 μm to about 150 μm, although it varies depending on the intended use.

The polyimide of the present invention may have preferably, but not limited to, a 5% weight loss temperature of 470° C. or more, more preferably 480° C. or more, particularly preferably 490° C. or more.

The polyimide of the present invention has excellent properties such as transparency, bending resistance and high heat resistance, and has a very low coefficient of linear thermal expansion up to a high temperature, and therefore the polyimide may be suitably used in the applications of transparent substrate for display, transparent substrate for touch panel, or substrate for solar battery.

One example of a method for producing a polyimide film/base laminate, or a polyimide film with the use of the polyimide precursor of the present invention will be described hereinafter. However, the method is not limited to the following method.

For example, a varnish of the polyimide precursor of the present invention is flow-cast on a base of ceramic (glass, silicon, or alumina), metal (copper, aluminum, or stainless steel), heat-resistant plastic film (polyimide), or the like, and dried at a temperature of 20° C. to 180° C., preferably 20° C. to 150° C., by the use of hot air or infrared ray in a vacuum, in an inert gas such as nitrogen, or in air. And then, the obtained polyimide precursor film is heated and imidized at a temperature of 200° C. to 500° C., more preferably about 250° C. to about 450° C., by the use of hot air or infrared ray in a vacuum, in an inert gas such as nitrogen, or in air, wherein the polyimide precursor film is on the base, or alternatively, the polyimide precursor film is peeled from the base and fixed at the edges, to provide a polyimide film/base laminate, or a polyimide film. The thermal imidization is preferably performed in a vacuum or in an inert gas so as to prevent oxidation and degradation of the obtained polyimide film. The thermal imidization may be performed in air if the thermal imidization temperature is not too high. At this point, the thickness of the polyimide film (the polyimide film layer, in the case of a polyimide film/base laminate) is preferably 1 μm to 250 μm, more preferably 1 μm to 150 μm, in view of the transportability in the subsequent steps.

The imidization reaction of the polyimide precursor may also be performed by chemical treatment in which the polyimide precursor is immersed in a solution containing a dehydrating/cyclizing agent such as acetic anhydride in the presence of a tertiary amine such as pyridine and triethylamine, instead of the thermal imidization by heat treatment as described above. Alternatively, a partially-imidized polyimide precursor may be prepared by adding the dehydrating/cyclizing agent to the varnish of the polyimide precursor in advance and stirring the varnish, and then flow-casting the varnish on a base and drying it. A polyimide film/base laminate, or a polyimide film may be obtained by further heating the partially-imidized polyimide precursor as described above.

A flexible conductive substrate may be obtained by forming a conductive layer on one surface or both surfaces of the polyimide film/base laminate or the polyimide film thus obtained.

A flexible conductive substrate may be obtained by the following methods, for example. As for the first method, the polyimide film is not peeled from the base in the "polyimide film/base" laminate, and a conductive layer of a conductive material (metal or metal oxide, conductive organic material, conductive carbon, or the like) is formed on the surface of the polyimide film by sputtering, vapor deposition, printing, or the like, to provide a conductive "conductive layer/polyimide film/base" laminate. And then, as necessary, the "conductive layer/polyimide film" laminate is peeled from the base, to provide a transparent and flexible conductive substrate which consists of the "conductive layer/polyimide film" laminate.

As for the second method, the polyimide film is peeled from the base in the "polyimide film/base" laminate to obtain the polyimide film, and then a conductive layer of a conductive material (metal or metal oxide, conductive organic material, conductive carbon, or the like) is formed on the surface of the polyimide film in the same way as in the first method, to provide a transparent and flexible conductive substrate which consists of the "conductive layer/polyimide film" laminate.

In the first and the second methods, a gas barrier layer against water vapor, oxygen, or the like, and an inorganic layer such as a light-controlling layer may be formed on the surface of the polyimide film by sputtering, vapor deposition, gel-sol process, or the like, as necessary, before the conductive layer is formed.

In addition, a circuit may be suitably formed on the conductive layer by photolithography process, various printing processes, ink-jet process, or the like.

The substrate of the present invention comprises a circuit of a conductive layer on a surface of a polyimide film formed of the polyimide of the present invention, optionally with a gas barrier layer or an inorganic layer therebetween, as necessary. The substrate is flexible, and has excellent transparency, bending resistance and heat resistance, and also has a very low coefficient of linear thermal expansion and excellent solvent resistance, and therefore a fine circuit may be easily formed thereon. Accordingly, the substrate may be suitably used as a substrate for display, touch panel, or solar battery.

More specifically, a flexible thin-film transistor is produced by further forming a transistor (inorganic transistor, or organic transistor) on the substrate by vapor deposition, various printing processes, ink-jet process, or the like, and is suitably used as a liquid crystal device for display device, an EL device, or a photoelectric device.

EXAMPLES

The present invention will be further described hereinafter with reference to Examples and Comparative Examples. However, the present invention is not limited to the following Examples.

In each of the following Examples, the evaluations were conducted by the following methods.

<Evaluation of Varnish of Polyimide Precursor>

[Logarithmic Viscosity]

A polyimide precursor solution at a concentration of 0.5 g/dL was prepared by diluting the varnish with the solvent used in the polymerization, and the logarithmic viscosity was determined by the measurement of the viscosity at 30° C. using an Ubbelohde viscometer.

<Evaluation of Polyimide Film>

[Light Transmittance at 400 nm, Total Light Transmittance]

The light transmittance at 400 nm and the total light transmittance (average light transmittance at 380 nm to 780 nm) of the polyimide film having a thickness of about 10 μm were measured using a MCPD-300 made by Otsuka Electronics Co., Ltd. The light transmittance at 400 nm and the total light transmittance of the film having a thickness of 10 μm were calculated from the measured light transmittance at 400 nm and the measured total light transmittance using the Lambert-Beer formula. The calculating formulas are shown below.

$$\mathrm{Log}_{10}(T_1/100) = 10/L \times (\mathrm{Log}_{10}(T_1'/100))$$

$$\mathrm{Log}_{10}(T_2/100) = 10/L \times (\mathrm{Log}_{10}(T_2'/100))$$

$T_1$: light transmittance at 400 nm of the polyimide film having a thickness of 10 μm (%)
$T_1'$: measured light transmittance at 400 nm (%)
$T_2$: total light transmittance of the polyimide film having a thickness of 10 μm (%)
$T_2'$: measured total light transmittance (%)
L: thickness of the polyimide film measured (μm)

Meanwhile, the light transmittance at 400 nm and the total light transmittance of the film having a thickness of 10 μm were calculated using the Lambert-Beer formula on the assumption that the reflectance was 10%. The calculating formulas are shown below.

$$\mathrm{Log}_{10}((T_3+10)/100) = 10/L \times (\mathrm{Log}_{10}((T_3'+10)/100))$$

$$\mathrm{Log}_{10}((T_4+10)/100) = 10/L \times (\mathrm{Log}_{10}((T_4'+10)/100))$$

$T_3$: light transmittance at 400 nm of the polyimide film having a thickness of 10 μm on the assumption that the reflectance was 10% (%)
$T_3'$: measured light transmittance at 400 nm (%)
$T_4$: total light transmittance of the polyimide film having a thickness of 10 μm on the assumption that the reflectance was 10% (%)
$T_4'$: measured total light transmittance (%)
L: thickness of the polyimide film measured (μm)

[Modulus of Elasticity, Elongation at Break]
The polyimide film having a thickness of about 10 μm was cut to the dumbbell shape of IEC450 standard, which was used as a test piece, and the initial modulus of elasticity and the elongation at break were measured at a distance between chucks of 30 mm and a tensile speed of 2 mm/min using a TENSILON made by Orientec Co., Ltd.

[Coefficient of Linear Thermal Expansion (CTE)]
The polyimide film having a thickness of about 10 μm was cut to a rectangle having a width of 4 mm, which was used as a test piece, and the test piece was heated to 500° C. at a distance between chucks of 15 mm, a load of 2 g and a temperature-increasing rate of 20° C./min using a TMA/SS6100 made by SII Nanotechnology Inc. The coefficient of linear thermal expansion from 50° C. to 400° C. was determined from the obtained TMA curve.

[5% Weight Loss Temperature]
The polyimide film having a thickness of about 10 μm was used as a test piece, and the test piece was heated from 25° C. to 600° C. at a temperature-increasing rate of 10° C./min in a flow of nitrogen using a thermogravimetric analyzer (Q5000IR) made by TA Instruments Inc. The 5% weight loss temperature was determined from the obtained weight curve.

The abbreviations, purities, etc. of the raw materials used in each of the following Examples are as follows.
[Diamine Component]
DABAN: 4,4'-diaminobenzanilide [purity: 99.90% (GC analysis)]
TFMB: 2,2'-bis(trifluoromethyl)benzidine [purity: 99.83% (GC analysis)]
PPD: p-phenylenediamine [purity: 99.9% (GC analysis)]
m-TD: m-tolidine [purity: 99.84% (GC analysis)]
BAPT: bis(4-aminophenyl)terephthalate [purity: 99.56% (LC analysis)]
FDA: 9,9-bis(4-aminophenyl)fluorene
4-APTP: N,N'-bis(4-aminophenyl)terephthalamide [purity: 99.95% (GC analysis)]
ODA: 4,4'-oxydianiline [purity: 99.9% (GC analysis)]
[Tetracarboxylic Acid Component]
CpODA: norbornane-2-spiro-α-cyclopentanone-α'-spiro-2''-norbornane-5,5'',6,6''-tetracarboxylic dianhydride
PMDA-HS: 1R,2S,4S,5R-cyclohexane tetracarboxylic dianhydride [purity as PMDA-HS: 92.7% (GC analysis); purity as hydrogenated pyromellitic dianhydride (mixture of stereoisomers): 99.9% (GC analysis)]
cis/cis-BTA-H: 1rC7-bicyclo[2.2.2]octane-2c,3c,5c,6c-tetracarboxylic-2,3:5,6-dianhydride [purity as cis/cis-BTA-H: 99.9% (GC analysis)]
[Silylating Agent]
BSA: N,O-bis(trimethylsilyl)acetamide
[Silica Dispersion]
ORGANOSILICA DMAc-ST; Silica solid content: 21.3 mass %
[Solvent]
DMAc: N,N-dimethylacetamide
NMP: N-methyl-2-pyrrolidone
[Purity of Solvent]
GC Analysis:
  Retention time of the main component (min) 14.28
  Area of the main component (%) 99.9929
  Peak area of the impurity having a shorter retention time (%) 0.0000
  Peak area of the impurity having a longer retention time (%) 0.0071
  Involatile component (mass %)<0.001
Light Transmittance:
  Light transmittance at 400 nm (%) 92
  Light transmittance at 400 nm after reflux (%) 92
Metal Content:
  Na (ppb) 150
  Fe (ppb)<2
  Cu (ppb)<2
  Mo (ppb)<1

The structural formulas of the tetracarboxylic acid components and the diamine components used in Examples and Comparative Examples are shown in Table 1.

TABLE 1

| tetracarboxylic dianhydride | diamine |
|---|---|
| CpODA | DABAN |

TABLE 1-continued

| tetracarboxylic dianhydride | diamine |
|---|---|
| PMDA-HS | PPD |
| cis/cis BTA-H | TFMB |
| | ODA |
| | FDA |
| | m-TD |
| | BAPT |
| | 4-APTP |

Example 1

2.27 g (10 mmol) of DABAN was placed in a reaction vessel, which was purged with nitrogen gas, and 17.41 g of N,N-dimethylacetamide was added thereto such that the total mass of loading monomers (total mass of the diamine component and the carboxylic acid component) was 26 mass %, and then the mixture was stirred at room temperature for 1 hour. 3.84 g (10 mmol) of CpODA was gradually added to the resulting solution. The mixture was stirred at room temperature for 12 hours, to provide a homogeneous and viscous polyimide precursor solution. The logarithmic viscosity of the obtained polyimide precursor was 1.0 dL/g.

The polyimide precursor solution, which was filtered through a PTFE membrane filter, was applied on a glass substrate, and then the polyimide precursor was thermally imidized by heating the polyimide precursor solution on the glass substrate from room temperature to 420° C. in a nitrogen atmosphere (oxygen concentration: 200 ppm or less), to provide a colorless and transparent polyimide film/glass laminate. Subsequently, the obtained polyimide film/glass laminate was immersed in water, and then the polyimide film was peeled from the glass and dried, to provide a polyimide film having a thickness of about 10 μm. The $T_1$ and $T_2$ of the obtained polyimide were 75% and 90%, respectively.

The results of the measurements of the properties of the polyimide film are shown in Table 2-1.

Example 2

3.20 g (10 mmol) of TFMB was placed in a reaction vessel, which was purged with nitrogen gas, and 18.12 g of N,N-dimethylacetamide was added thereto such that the total mass of loading monomers (total mass of the diamine component and the carboxylic acid component) was 28 mass %, and then the mixture was stirred at room temperature for 1 hour. 3.84 g (10 mmol) of CpODA was gradually added to the resulting solution. The mixture was stirred at room temperature for 12 hours, to provide a homogeneous and viscous polyimide precursor solution. The logarithmic viscosity of the obtained polyimide precursor was 0.6 dL/g.

The polyimide precursor solution, which was filtered through a PTFE membrane filter, was applied on a glass substrate, and then the polyimide precursor was thermally imidized by heating the polyimide precursor solution on the glass substrate from room temperature to 420° C. in a nitrogen atmosphere (oxygen concentration: 200 ppm or less), to provide a colorless and transparent polyimide film/glass laminate. Subsequently, the obtained polyimide film/glass laminate was immersed in water, and then the polyimide film was peeled from the glass and dried, to provide a polyimide film having a thickness of about 10 μm. The $T_1$ and $T_2$ of the obtained polyimide were 91% and 94%, respectively.

The results of the measurements of the properties of the polyimide film are shown in Table 2-1.

Example 3

1.08 g (10 mmol) of PPD was placed in a reaction vessel, which was purged with nitrogen gas, and 24.05 g of N,N-dimethylacetamide was added thereto such that the total mass of loading monomers (total mass of the diamine component and the carboxylic acid component) was 17 mass %, and then the mixture was stirred at room temperature for 1 hour. 3.84 g (10 mmol) of CpODA was gradually added to the resulting solution. The mixture was stirred at room temperature for 12 hours, to provide a homogeneous and viscous polyimide precursor solution. The logarithmic viscosity of the obtained polyimide precursor was 1.2 dL/g.

The polyimide precursor solution, which was filtered through a PTFE membrane filter, was applied on a glass substrate, and then the polyimide precursor was thermally imidized by heating the polyimide precursor solution on the glass substrate from room temperature to 420° C. in a nitrogen atmosphere (oxygen concentration: 200 ppm or less), to provide a colorless and transparent polyimide film/glass laminate. Subsequently, the obtained polyimide film/glass laminate was immersed in water, and then the polyimide film was peeled from the glass and dried, to provide a polyimide film having a thickness of about 10 μm. The $T_1$ and $T_2$ of the obtained polyimide were 85% and 90%, respectively.

The results of the measurements of the properties of the polyimide film are shown in Table 2-1.

Example 4

2.12 g (10 mmol) of m-TD was placed in a reaction vessel, which was purged with nitrogen gas, and 27.18 g of N,N-dimethylacetamide was added thereto such that the total mass of loading monomers (total mass of the diamine component and the carboxylic acid component) was 18 mass %, and then the mixture was stirred at room temperature for 1 hour. 3.84 g (10 mmol) of CpODA was gradually added to the resulting solution. The mixture was stirred at room temperature for 12 hours, to provide a homogeneous and viscous polyimide precursor solution. The logarithmic viscosity of the obtained polyimide precursor was 1.9 dL/g.

The polyimide precursor solution, which was filtered through a PTFE membrane filter, was applied on a glass substrate, and then the polyimide precursor was thermally imidized by heating the polyimide precursor solution on the glass substrate from room temperature to 420° C. in a nitrogen atmosphere (oxygen concentration: 200 ppm or less), to provide a colorless and transparent polyimide film/glass laminate. Subsequently, the obtained polyimide film/glass laminate was immersed in water, and then the polyimide film was peeled from the glass and dried, to provide a polyimide film having a thickness of about 10 μm. The $T_1$ and $T_2$ of the obtained polyimide were 89% and 92%, respectively.

The results of the measurements of the properties of the polyimide film are shown in Table 2-1.

Example 5

3.48 g (10 mmol) of BAPT was placed in a reaction vessel, which was purged with nitrogen gas, and 38.47 g of N,N-dimethylacetamide was added thereto such that the total mass of loading monomers (total mass of the diamine component and the carboxylic acid component) was 16 mass %, and then the mixture was stirred at room temperature for 1 hour. 3.84 g (10 mmol) of CpODA was gradually added to the resulting solution. The mixture was stirred at room temperature for 12 hours, to provide a homogeneous and viscous polyimide precursor solution. The logarithmic viscosity of the obtained polyimide precursor was 2.5 dL/g.

The polyimide precursor solution, which was filtered through a PTFE membrane filter, was applied on a glass substrate, and then the polyimide precursor was thermally imidized by heating the polyimide precursor solution on the glass substrate from room temperature to 420° C. in a nitrogen atmosphere (oxygen concentration: 200 ppm or less), to provide a colorless and transparent polyimide film/glass laminate. Subsequently, the obtained polyimide film/glass laminate was immersed in water, and then the polyimide film was peeled from the glass and dried, to provide a polyimide film having a thickness of about 10 μm. The $T_1$ and $T_2$ of the obtained polyimide were 74% and 86%, respectively.

The results of the measurements of the properties of the polyimide film are shown in Table 2-1.

Example 6

1.14 g (5 mmol) of DABAN and 1.60 g (5 mmol) of TFMB were placed in a reaction vessel, which was purged with nitrogen gas, and 16.34 g of N,N-dimethylacetamide was added thereto such that the total mass of loading monomers (total mass of the diamine component and the carboxylic acid component) was 25 mass %, and then the mixture was stirred at room temperature for 1 hour. 3.84 g (10 mmol) of CpODA was gradually added to the resulting solution. The mixture was stirred at room temperature for 12 hours, to provide a homogeneous and viscous polyimide precursor solution. The logarithmic viscosity of the obtained polyimide precursor was 0.2 dL/g.

The polyimide precursor solution, which was filtered through a PTFE membrane filter, was applied on a glass substrate, and then the polyimide precursor was thermally imidized by heating the polyimide precursor solution on the glass substrate from room temperature to 420° C. in a nitrogen atmosphere (oxygen concentration: 200 ppm or less), to provide a colorless and transparent polyimide film/glass laminate. Subsequently, the obtained polyimide film/glass laminate was immersed in water, and then the polyimide film was peeled from the glass and dried, to provide a polyimide film having a thickness of about 10 μm. The $T_1$ and $T_2$ of the obtained polyimide were 85% and 91%, respectively.

The results of the measurements of the properties of the polyimide film are shown in Table 2-1.

Example 7

1.59 g (7 mmol) of DABAN and 0.96 g (3 mmol) of TFMB were placed in a reaction vessel, which was purged with nitrogen gas, and 18.07 g of N,N-dimethylacetamide was added thereto such that the total mass of loading monomers (total mass of the diamine component and the carboxylic acid component) was 21 mass %, and then the mixture was stirred at room temperature for 1 hour. 3.84 g (10 mmol) of CpODA was gradually added to the resulting solution. The mixture was stirred at room temperature for 12 hours, to provide a homogeneous and viscous polyimide precursor solution. The logarithmic viscosity of the obtained polyimide precursor was 0.4 dL/g.

The polyimide precursor solution, which was filtered through a PTFE membrane filter, was applied on a glass substrate, and then the polyimide precursor was thermally imidized by heating the polyimide precursor solution on the glass substrate from room temperature to 420° C. in a nitrogen atmosphere (oxygen concentration: 200 ppm or less), to provide a colorless and transparent polyimide film/glass laminate. Subsequently, the obtained polyimide film/glass laminate was immersed in water, and then the polyimide film was peeled from the glass and dried, to provide a polyimide film having a thickness of about 10 μm. The $T_1$ and $T_2$ of the obtained polyimide were 86% and 92%, respectively.

The results of the measurements of the properties of the polyimide film are shown in Table 2-1.

Example 8

1.59 g (7 mmol) of DABAN and 0.32 g (3 mmol) of PPD were placed in a reaction vessel, which was purged with nitrogen gas, and 11.86 g of N,N-dimethylacetamide was added thereto such that the total mass of loading monomers (total mass of the diamine component and the carboxylic acid component) was 26 mass %, and then the mixture was stirred at room temperature for 1 hour. 3.84 g (10 mmol) of CpODA was gradually added to the resulting solution. The mixture was stirred at room temperature for 12 hours, to provide a homogeneous and viscous polyimide precursor solution. The logarithmic viscosity of the obtained polyimide precursor was 1.2 dL/g.

The polyimide precursor solution, which was filtered through a PTFE membrane filter, was applied on a glass substrate, and then the polyimide precursor was thermally imidized by heating the polyimide precursor solution on the glass substrate from room temperature to 420° C. in a nitrogen atmosphere (oxygen concentration: 200 ppm or less), to provide a colorless and transparent polyimide film/glass laminate. Subsequently, the obtained polyimide film/glass laminate was immersed in water, and then the polyimide film was peeled from the glass and dried, to provide a polyimide film having a thickness of about 10 μm. The $T_1$ and $T_2$ of the obtained polyimide were 84% and 92%, respectively.

The results of the measurements of the properties of the polyimide film are shown in Table 2-1.

Example 9

1.14 g (5 mmol) of DABAN and 0.54 g (5 mmol) of PPD were placed in a reaction vessel, which was purged with nitrogen gas, and 13.15 g of N,N-dimethylacetamide was added thereto such that the total mass of loading monomers (total mass of the diamine component and the carboxylic acid component) was 25 mass %, and then the mixture was stirred at room temperature for 1 hour. 3.84 g (10 mmol) of CpODA was gradually added to the resulting solution. The mixture was stirred at room temperature for 12 hours, to provide a homogeneous and viscous polyimide precursor solution. The logarithmic viscosity of the obtained polyimide precursor was 1.1 dL/g.

The polyimide precursor solution, which was filtered through a PTFE membrane filter, was applied on a glass substrate, and then the polyimide precursor was thermally imidized by heating the polyimide precursor solution on the glass substrate from room temperature to 420° C. in a nitrogen atmosphere (oxygen concentration: 200 ppm or less), to provide a colorless and transparent polyimide film/glass laminate. Subsequently, the obtained polyimide film/glass laminate was immersed in water, and then the polyimide film was peeled from the glass and dried, to provide a polyimide film having a thickness of about 10 μm. The $T_1$ and $T_2$ of the obtained polyimide were 85% and 92%, respectively.

The results of the measurements of the properties of the polyimide film are shown in Table 2-1.

Example 10

0.68 g (3 mmol) of DABAN and 0.76 g (7 mmol) of PPD were placed in a reaction vessel, which was purged with nitrogen gas, and 19.61 g of N,N-dimethylacetamide was added thereto such that the total mass of loading monomers (total mass of the diamine component and the carboxylic acid component) was 19 mass %, and then the mixture was stirred at room temperature for 1 hour. 3.84 g (10 mmol) of CpODA was gradually added to the resulting solution. The mixture was stirred at room temperature for 12 hours, to provide a homogeneous and viscous polyimide precursor solution. The logarithmic viscosity of the obtained polyimide precursor was 1.1 dL/g.

The polyimide precursor solution, which was filtered through a PTFE membrane filter, was applied on a glass substrate, and then the polyimide precursor was thermally imidized by heating the polyimide precursor solution on the glass substrate from room temperature to 420° C. in a nitrogen atmosphere (oxygen concentration: 200 ppm or less), to provide a colorless and transparent polyimide film/glass laminate. Subsequently, the obtained polyimide film/glass laminate was immersed in water, and then the polyimide film was peeled from the glass and dried, to provide a polyimide film having a thickness of about 10 μm. The $T_1$ and $T_2$ of the obtained polyimide were 86% and 92%, respectively.

The results of the measurements of the properties of the polyimide film are shown in Table 2-1.

Example 11

3.46 g (10 mmol) of 4-APTP was placed in a reaction vessel, which was purged with nitrogen gas, and 48.85 g of N-methyl-2-pyrrolidone was added thereto such that the total mass of loading monomers (total mass of the diamine component and the carboxylic acid component) was 13 mass %, and then the mixture was stirred at room temperature for 1 hour. 3.84 g (10 mmol) of CpODA was gradually added to the resulting solution. The mixture was stirred at room temperature for 12 hours, to provide a homogeneous and viscous polyimide precursor solution.

The polyimide precursor solution, which was filtered through a PTFE membrane filter, was applied on a glass substrate, and then the polyimide precursor was thermally imidized by heating the polyimide precursor solution on the glass substrate from room temperature to 420° C. in a nitrogen atmosphere (oxygen concentration: 200 ppm or less), to provide a colorless and transparent polyimide film/glass laminate. Subsequently, the obtained polyimide film/glass laminate was immersed in water, and then the polyimide film was peeled from the glass and dried, to provide a polyimide film having a thickness of about 10 μm.

The results of the measurements of the properties of the polyimide film are shown in Table 2-1.

Example 12

1.14 g (5 mmol) of DABAN and 0.54 g (5 mmol) of PPD were placed in a reaction vessel, which was purged with nitrogen gas, and 22.08 g of N-methyl-2-pyrrolidone was added thereto such that the total mass of loading monomers (total mass of the diamine component and the carboxylic acid component) was 20 mass %, and then the mixture was stirred at room temperature for 1 hour. 3.84 g (10 mmol) of CpODA was gradually added to the resulting solution. The mixture was stirred at room temperature for 12 hours, to provide a homogeneous and viscous polyimide precursor solution.

The polyimide solution, which was filtered through a PTFE membrane filter, was applied on a glass substrate, and then the polyimide solution on the glass substrate was heated from room temperature to 420° C. in a nitrogen atmosphere (oxygen concentration: 200 ppm or less), to provide a colorless and transparent polyimide film/glass laminate. Subsequently, the obtained polyimide film/glass laminate was immersed in water, and then the polyimide film was peeled from the glass and dried, to provide a polyimide film having a thickness of about 10 μm.

The results of the measurements of the properties of the polyimide film are shown in Table 2-1.

Example 13

1.60 g (5 mmol) of TFMB and 0.54 g (5 mmol) of PPD were placed in a reaction vessel, which was purged with nitrogen gas, and 20.02 g of N,N-dimethylacetamide was added thereto such that the total mass of loading monomers (total mass of the diamine component and the carboxylic acid component) was 23 mass %, and then the mixture was stirred at room temperature for 1 hour. 3.84 g (10 mmol) of CpODA was gradually added to the resulting solution. The mixture was stirred at room temperature for 12 hours, to provide a homogeneous and viscous polyimide precursor solution.

The polyimide solution, which was filtered through a PTFE membrane filter, was applied on a glass substrate, and then the polyimide solution on the glass substrate was heated from room temperature to 420° C. in a nitrogen atmosphere (oxygen concentration: 200 ppm or less), to provide a colorless and transparent polyimide film/glass laminate. Subsequently, the obtained polyimide film/glass laminate was immersed in water, and then the polyimide film was peeled from the glass and dried, to provide a polyimide film having a thickness of about 10 μm.

The results of the measurements of the properties of the polyimide film are shown in Table 2-1.

Example 14

0.96 g (3 mmol) of TFMB and 0.76 g (7 mmol) of PPD were placed in a reaction vessel, which was purged with nitrogen gas, and 18.61 g of N,N-dimethylacetamide was added thereto such that the total mass of loading monomers (total mass of the diamine component and the carboxylic acid component) was 23 mass %, and then the mixture was stirred at room temperature for 1 hour. 3.84 g (10 mmol) of CpODA was gradually added to the resulting solution. The mixture was stirred at room temperature for 12 hours, to provide a homogeneous and viscous polyimide precursor solution.

The polyimide solution, which was filtered through a PTFE membrane filter, was applied on a glass substrate, and then the polyimide solution on the glass substrate was heated from room temperature to 420° C. in a nitrogen atmosphere (oxygen concentration: 200 ppm or less), to provide a colorless and transparent polyimide film/glass laminate. Subsequently, the obtained polyimide film/glass laminate was immersed in water, and then the polyimide film was peeled from the glass and dried, to provide a polyimide film having a thickness of about 10 μm.

The results of the measurements of the properties of the polyimide film are shown in Table 2-1.

Example 15

0.91 g (4 mmol) of DABAN, 0.22 g (2 mmol) of PPD and 1.28 g (4 mmol) of TFMB were placed in a reaction vessel, which was purged with nitrogen gas, and 25.00 g of N,N-dimethylacetamide was added thereto such that the total mass of loading monomers (total mass of the diamine component and the carboxylic acid component) was 20 mass %, and then the mixture was stirred at room temperature for 1 hour. 3.84 g (10 mmol) of CpODA was gradually added to the resulting solution. The mixture was stirred at room temperature for 12 hours, to provide a homogeneous and viscous polyimide precursor solution.

The polyimide solution, which was filtered through a PTFE membrane filter, was applied on a glass substrate, and then the polyimide solution on the glass substrate was heated from room temperature to 420° C. in a nitrogen atmosphere (oxygen concentration: 200 ppm or less), to provide a colorless and transparent polyimide film/glass laminate.

Subsequently, the obtained polyimide film/glass laminate was immersed in water, and then the polyimide film was peeled from the glass and dried, to provide a polyimide film having a thickness of about 10 μm.

The results of the measurements of the properties of the polyimide film are shown in Table 2-2.

Example 16

0.68 g (3 mmol) of DABAN, 0.22 g (2 mmol) of PPD and 1.60 g (5 mmol) of TFMB were placed in a reaction vessel, which was purged with nitrogen gas, and 25.36 g of N,N-dimethylacetamide was added thereto such that the total mass of loading monomers (total mass of the diamine component and the carboxylic acid component) was 20 mass %, and then the mixture was stirred at room temperature for 1 hour. 3.84 g (10 mmol) of CpODA was gradually added to the resulting solution. The mixture was stirred at room temperature for 12 hours, to provide a homogeneous and viscous polyimide precursor solution.

The polyimide solution, which was filtered through a PTFE membrane filter, was applied on a glass substrate, and then the polyimide solution on the glass substrate was heated from room temperature to 420° C. in a nitrogen atmosphere (oxygen concentration: 200 ppm or less), to provide a colorless and transparent polyimide film/glass laminate. Subsequently, the obtained polyimide film/glass laminate was immersed in water, and then the polyimide film was peeled from the glass and dried, to provide a polyimide film having a thickness of about 10 μm.

The results of the measurements of the properties of the polyimide film are shown in Table 2-2.

Example 17

0.91 g (4 mmol) of DABAN, 0.35 g (1 mmol) of FDA and 1.60 g (5 mmol) of TFMB were placed in a reaction vessel, which was purged with nitrogen gas, and 30.52 g of N-methyl-2-pyrrolidone was added thereto such that the total mass of loading monomers (total mass of the diamine component and the carboxylic acid component) was 18 mass %, and then the mixture was stirred at room temperature for 1 hour. 3.84 g (10 mmol) of CpODA was gradually added to the resulting solution. The mixture was stirred at room temperature for 12 hours, to provide a homogeneous and viscous polyimide precursor solution.

The polyimide solution, which was filtered through a PTFE membrane filter, was applied on a glass substrate, and then the polyimide solution on the glass substrate was heated from room temperature to 420° C. in a nitrogen atmosphere (oxygen concentration: 200 ppm or less), to provide a colorless and transparent polyimide film/glass laminate. Subsequently, the obtained polyimide film/glass laminate was immersed in water, and then the polyimide film was peeled from the glass and dried, to provide a polyimide film having a thickness of about 10 μm.

The results of the measurements of the properties of the polyimide film are shown in Table 2-2.

Example 18

2.05 g (9 mmol) of DABAN and 0.35 g (1 mmol) of FDA were placed in a reaction vessel, which was purged with nitrogen gas, and 28.43 g of N-methyl-2-pyrrolidone was added thereto such that the total mass of loading monomers (total mass of the diamine component and the carboxylic acid component) was 18 mass %, and then the mixture was stirred at room temperature for 1 hour. 3.84 g (10 mmol) of CpODA was gradually added to the resulting solution. The mixture was stirred at room temperature for 12 hours, to provide a homogeneous and viscous polyimide precursor solution.

The polyimide solution, which was filtered through a PTFE membrane filter, was applied on a glass substrate, and then the polyimide solution on the glass substrate was heated from room temperature to 420° C. in a nitrogen atmosphere (oxygen concentration: 200 ppm or less), to provide a colorless and transparent polyimide film/glass laminate. Subsequently, the obtained polyimide film/glass laminate was immersed in water, and then the polyimide film was peeled from the glass and dried, to provide a polyimide film having a thickness of about 10 μm.

The results of the measurements of the properties of the polyimide film are shown in Table 2-2.

Example 19

3.12 g (9 mmol) of 4-APTP and 0.35 g (1 mmol) of FDA were placed in a reaction vessel, which was purged with nitrogen gas, and 48.92 g of N-methyl-2-pyrrolidone was added thereto such that the total mass of loading monomers (total mass of the diamine component and the carboxylic acid component) was 13 mass %, and then the mixture was stirred at room temperature for 1 hour. 3.84 g (10 mmol) of CpODA was gradually added to the resulting solution. The mixture was stirred at room temperature for 12 hours, to provide a homogeneous and viscous polyimide precursor solution.

The polyimide solution, which was filtered through a PTFE membrane filter, was applied on a glass substrate, and then the polyimide solution on the glass substrate was heated from room temperature to 420° C. in a nitrogen atmosphere (oxygen concentration: 200 ppm or less), to provide a colorless and transparent polyimide film/glass laminate. Subsequently, the obtained polyimide film/glass laminate was immersed in water, and then the polyimide film was peeled from the glass and dried, to provide a polyimide film having a thickness of about 10 μm.

The results of the measurements of the properties of the polyimide film are shown in Table 2-2.

Example 20

2.27 g (10 mmol) of DABAN was placed in a reaction vessel, which was purged with nitrogen gas, and 5.88 g of ORGANOSILICASOL DMAc-ST made by Nissan Chemical Industries, Ltd., and 19.83 g of N,N-dimethylacetamide were added thereto, and then the mixture was stirred at room temperature for 1 hour. 3.84 g (10 mmol) of CpODA was gradually added to the resulting solution. The mixture was stirred at room temperature for 12 hours, to provide a homogeneous and viscous polyimide precursor solution.

The polyimide precursor solution, which was filtered through a PTFE membrane filter, was applied on a glass substrate, and then the polyimide precursor was thermally imidized by heating the polyimide precursor solution on the glass substrate from room temperature to 420° C. in a nitrogen atmosphere (oxygen concentration: 200 ppm or less), to provide a colorless and transparent polyimide film/glass laminate. Subsequently, the obtained polyimide film/glass laminate was immersed in water, and then the polyimide film was peeled from the glass and dried, to provide a polyimide film having a thickness of about 10 μm. The $T_1$ and $T_2$ of the obtained polyimide were 79% and 90%, respectively.

The results of the measurements of the properties of the polyimide film are shown in Table 2-2.

Example 21

2.27 g (10 mmol) of DABAN was placed in a reaction vessel, which was purged with nitrogen gas, and 11.32 g of ORGANOSILICASOL DMAc-ST made by Nissan Chemical Industries, Ltd., and 15.55 g of N,N-dimethylacetamide were added thereto, and then the mixture was stirred at room temperature for 1 hour. 3.84 g (10 mmol) of CpODA was gradually added to the resulting solution. The mixture was stirred at room temperature for 12 hours, to provide a homogeneous and viscous polyimide precursor solution.

The polyimide precursor solution, which was filtered through a PTFE membrane filter, was applied on a glass substrate, and then the polyimide precursor was thermally imidized by heating the polyimide precursor solution on the glass substrate from room temperature to 420° C. in a nitrogen atmosphere (oxygen concentration: 200 ppm or less), to provide a colorless and transparent polyimide film/glass laminate. Subsequently, the obtained polyimide film/glass laminate was immersed in water, and then the polyimide film was peeled from the glass and dried, to provide a polyimide film having a thickness of about 10 μm. The $T_1$ and $T_2$ of the obtained polyimide were 83% and 92%, respectively.

The results of the measurements of the properties of the polyimide film are shown in Table 2-2.

Example 22

3.20 g (10 mmol) of TFMB was placed in a reaction vessel, which was purged with nitrogen gas, and 3.60 g of ORGANOSILICASOL DMAc-ST made by Nissan Chemical Industries, Ltd., and 25.35 g of N,N-dimethylacetamide were added thereto, and then the mixture was stirred at room temperature for 1 hour. 3.84 g (10 mmol) of CpODA was gradually added to the resulting solution. The mixture was stirred at room temperature for 12 hours, to provide a homogeneous and viscous polyimide precursor solution.

The polyimide precursor solution, which was filtered through a PTFE membrane filter, was applied on a glass substrate, and then the polyimide precursor was thermally imidized by heating the polyimide precursor solution on the glass substrate from room temperature to 420° C. in a nitrogen atmosphere (oxygen concentration: 200 ppm or less), to provide a colorless and transparent polyimide film/glass laminate. Subsequently, the obtained polyimide film/glass laminate was immersed in water, and then the polyimide film was peeled from the glass and dried, to provide a polyimide film having a thickness of about 10 μm. The $T_1$ and $T_2$ of the obtained polyimide were 89% and 94%, respectively.

The results of the measurements of the properties of the polyimide film are shown in Table 2-2.

Example 23

3.20 g (10 mmol) of TFMB was placed in a reaction vessel, which was purged with nitrogen gas, and 7.61 g of ORGANOSILICASOL DMAc-ST made by Nissan Chemical Industries, Ltd., and 22.20 g of N,N-dimethylacetamide were added thereto, and then the mixture was stirred at room temperature for 1 hour. 3.84 g (10 mmol) of CpODA was gradually added to the resulting solution. The mixture was stirred at room temperature for 12 hours, to provide a homogeneous and viscous polyimide precursor solution.

The polyimide precursor solution, which was filtered through a PTFE membrane filter, was applied on a glass substrate, and then the polyimide precursor was thermally imidized by heating the polyimide precursor solution on the glass substrate from room temperature to 420° C. in a nitrogen atmosphere (oxygen concentration: 200 ppm or less), to provide a colorless and transparent polyimide film/glass laminate. Subsequently, the obtained polyimide film/glass laminate was immersed in water, and then the polyimide film was peeled from the glass and dried, to provide a polyimide film having a thickness of about 10 μm. The $T_1$ and $T_2$ of the obtained polyimide were 86% and 94%, respectively.

The results of the measurements of the properties of the polyimide film are shown in Table 2-2.

Example 24

5.00 g of the polyimide precursor solution obtained in Example 8 was placed in a reaction vessel, which was purged with nitrogen gas, and 0.93 g of N,O-bis(trimethylsilyl)acetamide was added thereto, and then the mixture was stirred at room temperature for 12 hours, to provide a homogeneous and viscous polyimide precursor solution.

The polyimide solution, which was filtered through a PTFE membrane filter, was applied on a glass substrate, and then the polyimide solution on the glass substrate was heated from room temperature to 420° C. in a nitrogen atmosphere (oxygen concentration: 200 ppm or less), to provide a colorless and transparent polyimide film/glass laminate. Subsequently, the obtained polyimide film/glass laminate was immersed in water, and then the polyimide film was peeled from the glass and dried, to provide a polyimide film having a thickness of about 10 μm. The $T_1$ and $T_2$ of the obtained polyimide were 78% and 87%, respectively.

The results of the measurements of the properties of the polyimide film are shown in Table 2-2.

Example 25

0.91 g (4 mmol) of DABAN, 0.54 g (5 mmol) of PPD and 0.32 g (1 mmol) of TFMB were placed in a reaction vessel, which was purged with nitrogen gas, and 25.56 g of N-methyl-2-pyrrolidone was added thereto such that the total mass of loading monomers (total mass of the diamine component and the carboxylic acid component) was 18 mass %, and then the mixture was stirred at room temperature for 1 hour. 3.84 g (10 mmol) of CpODA was gradually added to the resulting solution. The mixture was stirred at room temperature for 12 hours, to provide a homogeneous and viscous polyimide precursor solution.

The polyimide solution, which was filtered through a PTFE membrane filter, was applied on a glass substrate, and then the polyimide solution on the glass substrate was heated from room temperature to 420° C. in a nitrogen atmosphere (oxygen concentration: 200 ppm or less), to provide a colorless and transparent polyimide film/glass laminate. Subsequently, the obtained polyimide film/glass laminate was immersed in water, and then the polyimide film was peeled from the glass and dried, to provide a polyimide film having a thickness of about 10 μm.

Example 26

0.68 g (3 mmol) of DABAN, 0.65 g (6 mmol) of PPD and 0.32 g (1 mmol) of TFMB were placed in a reaction vessel, which was purged with nitrogen gas, and 25.01 g of N-methyl-2-pyrrolidone was added thereto such that the total mass of loading monomers (total mass of the diamine component and the carboxylic acid component) was 18 mass %, and then the mixture was stirred at room temperature for 1 hour. 3.84 g (10 mmol) of CpODA was gradually added to the resulting solution. The mixture was stirred at room temperature for 12 hours, to provide a homogeneous and viscous polyimide precursor solution.

The polyimide solution, which was filtered through a PTFE membrane filter, was applied on a glass substrate, and then the polyimide solution on the glass substrate was heated from room temperature to 420° C. in a nitrogen atmosphere (oxygen concentration: 200 ppm or less), to provide a colorless and transparent polyimide film/glass laminate. Subsequently, the obtained polyimide film/glass laminate was immersed in water, and then the polyimide film was peeled from the glass and dried, to provide a polyimide film having a thickness of about 10 μm.

The results of the measurements of the properties of the polyimide film are shown in Table 2-2.

Example 27

0.91 g (4 mmol) of DABAN, 0.54 g (5 mmol) of PPD and 0.20 g (1 mmol) of ODA were placed in a reaction vessel, which was purged with nitrogen gas, and 25.01 g of N-methyl-2-pyrrolidone was added thereto such that the total mass of loading monomers (total mass of the diamine component and the carboxylic acid component) was 18 mass %, and then the mixture was stirred at room temperature for 1 hour. 3.84 g (10 mmol) of CpODA was gradually added to the resulting solution. The mixture was stirred at room temperature for 12 hours, to provide a homogeneous and viscous polyimide precursor solution.

The polyimide solution, which was filtered through a PTFE membrane filter, was applied on a glass substrate, and then the polyimide solution on the glass substrate was heated from room temperature to 420° C. in a nitrogen atmosphere (oxygen concentration: 200 ppm or less), to provide a colorless and transparent polyimide film/glass laminate. Subsequently, the obtained polyimide film/glass laminate was immersed in water, and then the polyimide film was peeled from the glass and dried, to provide a polyimide film having a thickness of about 10 μm.

The results of the measurements of the properties of the polyimide film are shown in Table 2-2.

Example 28

0.68 g (3 mmol) of DABAN, 0.65 g (6 mmol) of PPD and 0.20 g (1 mmol) of ODA were placed in a reaction vessel, which was purged with nitrogen gas, and 24.46 g of N-methyl-2-pyrrolidone was added thereto such that the total mass of loading monomers (total mass of the diamine component and the carboxylic acid component) was 18 mass %, and then the mixture was stirred at room temperature for 1 hour. 3.84 g (10 mmol) of CpODA was gradually added to the resulting solution. The mixture was stirred at room temperature for 12 hours, to provide a homogeneous and viscous polyimide precursor solution.

The polyimide solution, which was filtered through a PTFE membrane filter, was applied on a glass substrate, and then the polyimide solution on the glass substrate was heated from room temperature to 420° C. in a nitrogen atmosphere (oxygen concentration: 200 ppm or less), to provide a colorless and transparent polyimide film/glass laminate. Subsequently, the obtained polyimide film/glass laminate was immersed in water, and then the polyimide film was peeled from the glass and dried, to provide a polyimide film having a thickness of about 10 μm.

The results of the measurements of the properties of the polyimide film are shown in Table 2-2.

Comparative Example 11

2.00 g (10 mmol) of ODA was placed in a reaction vessel, which was purged with nitrogen gas, and 23.39 g of N,N-dimethylacetamide was added thereto such that the total mass of loading monomers (total mass of the diamine component and the carboxylic acid component) was 20 mass %, and then the mixture was stirred at room temperature for 1 hour. 3.84 g (10 mmol) of CpODA was gradually added to the resulting solution. The mixture was stirred at room temperature for 12 hours, to provide a homogeneous and viscous polyimide precursor solution. The logarithmic viscosity of the obtained polyimide precursor was 1.6 dL/g.

The polyimide precursor solution, which was filtered through a PTFE membrane filter, was applied on a glass substrate, and then the polyimide precursor was thermally imidized by heating the polyimide precursor solution on the glass substrate from room temperature to 420° C. in a nitrogen atmosphere (oxygen concentration: 200 ppm or less), to provide a colorless and transparent polyimide film/glass laminate. Subsequently, the obtained polyimide film/glass laminate was immersed in water, and then the polyimide film was peeled from the glass and dried, to provide a polyimide film having a thickness of about 10 μm. The $T_1$ and $T_2$ of the obtained polyimide were 82% and 89%, respectively.

The results of the measurements of the properties of the polyimide film are shown in Table 2-3.

Comparative Example 2

2.00 g (10 mmol) of ODA was placed in a reaction vessel, which was purged with nitrogen gas, and 20.70 g of N,N-dimethylacetamide was added thereto such that the total mass of loading monomers (total mass of the diamine component and the carboxylic acid component) was 17 mass %, and then the mixture was stirred at room temperature for 1 hour. 2.24 g (10 mmol) of PMDA-HS was gradually added to the resulting solution. The mixture was stirred at room temperature for 12 hours, to provide a homogeneous and viscous polyimide precursor solution. The logarithmic viscosity of the obtained polyimide precursor was 1.0 dL/g.

The polyimide precursor solution, which was filtered through a PTFE membrane filter, was applied on a glass substrate, and then the polyimide precursor was thermally imidized by heating the polyimide precursor solution on the glass substrate from room temperature to 420° C. in a nitrogen atmosphere (oxygen concentration: 200 ppm or less), to provide a colorless and transparent polyimide film/glass laminate. Subsequently, the obtained polyimide film/glass laminate was immersed in water, and then the polyimide film was peeled from the glass and dried, to provide a polyimide film having a thickness of about 10 μm. The $T_1$ and $T_2$ of the obtained polyimide were 86% and 89%, respectively.

The results of the measurements of the properties of the polyimide film are shown in Table 2-3.

Comparative Example 3

2.00 g (10 mmol) of ODA was placed in a reaction vessel, which was purged with nitrogen gas, and 20.50 g of N,N-dimethylacetamide was added thereto such that the total mass of loading monomers (total mass of the diamine component and the carboxylic acid component) was 18 mass %, and then the mixture was stirred at room temperature for 1 hour. 2.50 g (10 mmol) of cis/cis BTA-H was gradually added to the resulting solution. The mixture was stirred at room temperature for 12 hours, to provide a homogeneous and viscous polyimide precursor solution. The logarithmic viscosity of the obtained polyimide precursor was 0.6 dL/g.

The polyimide precursor solution, which was filtered through a PTFE membrane filter, was applied on a glass substrate, and then the polyimide precursor was thermally imidized by heating the polyimide precursor solution on the glass substrate from room temperature to 420° C. in a nitrogen atmosphere (oxygen concentration: 200 ppm or less), to provide a colorless and transparent polyimide film/glass laminate. Subsequently, the obtained polyimide film/glass laminate was immersed in water, and then the polyimide film was peeled from the glass and dried, to provide a polyimide film having a thickness of about 10 μm. The $T_1$ and $T_2$ of the obtained polyimide were 84% and 88%, respectively.

The results of the measurements of the properties of the polyimide film are shown in Table 2-3.

TABLE 2-1

| | | Example 1 | Example 2 | Example 3 | Example 4 | Example 5 | Example 6 | Example 7 |
|---|---|---|---|---|---|---|---|---|
| Polyimide precursor | | | | | | | | |
| Tetracarboxylic acid component (mmol) | CpODA | 10 | 10 | 10 | 10 | 10 | 10 | 10 |
| | PMDA-HS | | | | | | | |
| | cis/cisBTA-H | | | | | | | |
| Diamine component (mmol) | DABAN | 10 | | | | | 5 | 7 |
| | TFMB | | 10 | | | | 5 | 3 |
| | PPD | | | 10 | | | | |
| | m-TD | | | | 10 | | | |
| | BAPT | | | | | 10 | | |
| | 4-APTP | | | | | | | |
| | FDA | | | | | | | |
| | ODA | | | | | | | |
| Silylating agent (mmol) | BSA | | | | | | | |
| Silica content in film (vol %) | | | | | | | | |
| Polyimide film | | | | | | | | |
| Light transmittance at 400 nm, $T_3$ (%) | | 72 | 87 | 84 | 86 | 73 | 83 | 82 |
| Total light transmittance, $T_4$ (%) | | 83 | 90 | 89 | 88 | 84 | 89 | 87 |
| Modulus of elasticity (GPa) | | 5.2 | 3.0 | 3.3 | 4.4 | 5.0 | 3.4 | 3.6 |
| Elongation at break (%) | | 13 | 26 | 5 | 30 | 9 | 35 | 24 |
| Coefficient of linear thermal expansion (ppm/K) (50-400° C.) | | 16 | 76 | 29 | 66 | 27 | 62 | 48 |
| 5% weight loss temperature (° C.) | | 497 | 481 | 494 | 474 | 475 | 483 | 484 |

| | | Example 8 | Example 9 | Example 10 | Example 11 | Example 12 | Example 13 | Example 14 |
|---|---|---|---|---|---|---|---|---|
| Polyimide precursor | | | | | | | | |
| Tetracarboxylic acid component (mmol) | CpODA | 10 | 10 | 10 | 10 | 10 | 10 | 10 |
| | PMDA-HS | | | | | | | |
| | cis/cisBTA-H | | | | | | | |
| Diamine component (mmol) | DABAN | 7 | 5 | 3 | | 5 | | |
| | TFMB | | | | | | 5 | 3 |
| | PPD | 3 | 5 | 7 | | 5 | 5 | 7 |
| | m-TD | | | | | | | |
| | BAPT | | | | | | | |

TABLE 2-1-continued

|  |  |  |  |  |  |  |  |
|---|---|---|---|---|---|---|---|
|  | 4-APTP |  |  |  | 10 |  |  |
|  | FDA |  |  |  |  |  |  |
|  | ODA |  |  |  |  |  |  |
| Silylating agent (mmol) | BSA |  |  |  |  |  |  |
| Silica content in film (vol %) |  |  |  |  |  |  |  |
| Polyimide film |  |  |  |  |  |  |  |
| Light transmittance at 400 nm, $T_3$ (%) |  | 80 | 82 | 83 | 52 | 82 | 85 | 83 |
| Total light transmittance, $T_4$ (%) |  | 86 | 88 | 87 | 85 | 87 | 89 | 89 |
| Modulus of elasticity (GPa) |  | 5.5 | 4.0 | 4.7 | 5.7 | 4.1 | — | — |
| Elongation at break (%) |  | 15 | 18 | 13 | 15 | 11 | — | — |
| Coefficient of linear thermal expansion (ppm/K) (50-400° C.) |  | 24 | 26 | 30 | 11 | 29 | 70 | 64 |
| 5% weight loss temperature (° C.) |  | 496 | 496 | 496 | 504 | 503 | 489 | 492 |

TABLE 2-2

|  |  | Example 15 | Example 16 | Example 17 | Example 18 | Example 19 | Example 20 | Example 21 |
|---|---|---|---|---|---|---|---|---|
| Polyimide precursor |  |  |  |  |  |  |  |  |
| Tetra-carboxylic acid component (mmol) | CpODA | 10 | 10 | 10 | 10 | 10 | 10 | 10 |
|  | PMDA-HS |  |  |  |  |  |  |  |
|  | cis/cisBTA-H |  |  |  |  |  |  |  |
| Diamine component (mmol) | DABAN | 4 | 3 | 4 | 9 |  | 10 | 10 |
|  | TFMB | 4 | 5 | 5 |  |  |  |  |
|  | PPD | 2 | 2 |  |  |  |  |  |
|  | m-TD |  |  |  |  |  |  |  |
|  | BAPT |  |  |  |  |  |  |  |
|  | 4-APTP |  |  |  |  | 9 |  |  |
|  | FDA |  |  | 1 | 1 | 1 |  |  |
|  | ODA |  |  |  |  |  |  |  |
| Silylating agent (mmol) | BSA |  |  |  |  |  |  |  |
| Silica content in film (vol %) |  |  |  |  |  |  | 9 | 16 |
| Polyimide film |  |  |  |  |  |  |  |  |
| Light transmittance at 400 nm, $T_3$ (%) |  | 84 | 83 | 83 | 78 | 60 | 77 | 80 |
| Total light transmittance, $T_4$ (%) |  | 88 | 88 | 87 | 87 | 85 | 87 | 88 |
| Modulus of elasticity (GPa) |  | 3.3 | 3.2 | 3.3 | 4.1 | 5.2 | 5.9 | 6.7 |
| Elongation at break (%) |  | 23 | 11 | 8 | 4 | 14 | 6 | 3 |
| Coefficient of linear thermal expansion (ppm/K) (50-400° C.) |  | 40 | 71 | 40 | 29 | 11 | 23 | 26 |
| 5% weight loss temperature (° C.) |  | — | — | 500 | 500 | 501 | 499 | 500 |

|  |  | Example 22 | Example 23 | Example 24 | Example 25 | Example 26 | Example 27 | Example 28 |
|---|---|---|---|---|---|---|---|---|
| Polyimide precursor |  |  |  |  |  |  |  |  |
| Tetra-carboxylic acid component (mmol) | CpODA | 10 | 10 | 10 | 10 | 10 | 10 | 10 |
|  | PMDA-HS |  |  |  |  |  |  |  |
|  | cis/cisBTA-H |  |  |  |  |  |  |  |

TABLE 2-2-continued

|  |  |  |  |  |  |  |  |  |
|---|---|---|---|---|---|---|---|---|
| Diamine component (mmol) | DABAN | | | 7 | 4 | 3 | 4 | 3 |
| | TFMB | 10 | 10 | | 1 | 1 | | |
| | PPD | | | 3 | 5 | 6 | 5 | 6 |
| | m-TD | | | | | | | |
| | BAPT | | | | | | | |
| | 4-APTP | | | | | | | |
| | FDA | | | | | | | |
| | ODA | | | | | | 1 | 1 |
| Silylating agent (mmol) | BSA | | | 20 | | | | |
| Silica content in film (vol %) | | 5 | 10 | 20 | | | | |
| Polyimide film | | | | | | | | |
| Light transmittance at 400 nm, $T_3$ (%) | | 85 | 82 | 77 | 77 | 77 | 75 | 77 |
| Total light transmittance, $T_4$ (%) | | 89 | 88 | 87 | 86 | 87 | 86 | 86 |
| Modulus of elasticity (GPa) | | 3.5 | 4.3 | 4.4 | 4.8 | 4.8 | 4.7 | 4.3 |
| Elongation at break (%) | | 2 | 1 | 23.5 | 8 | 6 | 11 | 7 |
| Coefficient of linear thermal expansion (ppm/K) (50-400° C.) | | 76 | 69 | 22 | 27 | 24 | 27 | 27 |
| 5% weight loss temperature (° C.) | | 484 | 488 | 491 | 492 | 493 | 496 | 495 |

— Not conducted

TABLE 2-3

|  |  | Comparative Example 1 | Comparative Example 2 | Comparative Example 3 |
|---|---|---|---|---|
| Polyimide precursor | | | | |
| Tetracarboxylic acid component (mmol) | CpODA | 10 | | |
| | PMDA-HS | | 10 | |
| | cis/cisBTA-H | | | 10 |
| Diamine component (mmol) | DABAN | | | |
| | TFMB | | | |
| | PPD | | | |
| | m-TD | | | |
| | BAPT | | | |
| | 4-APTP | | | |
| | FDA | | | |
| | ODA | 10 | 10 | 10 |
| Silylating agent (mmol) | BSA | | | |
| Silica content in film (vol %) | | | | |
| Polyimide film | | | | |
| Light transmittance at 400 nm, $T_3$ (%) | | 79 | 86 | 84 |
| Total light transmittance, $T_4$ (%) | | 86 | 89 | 88 |
| Modulus of elasticity (GPa) | | 2.3 | 3.1 | 2.2 |
| Elongation at break (%) | | 78 | 73 | 10 |
| Coefficient of linear thermal expansion (ppm/K) (50-400° C.) | | 117 | >1000 | >1000 |
| 5% weight loss temperature (° C.) | | 490 | 467 | 502 |

As can be seen from the results shown in Tables 2-1 to 2-3, the polyimides of the present invention (Examples 1 to 28) have a small coefficient of linear thermal expansion up to a high temperature, specifically from 50° C. to 400° C., as compared with Comparative Examples 1 to 3.

When DABAN, PPD or BAPT is used as the diamine component, in particular, the coefficient of linear thermal expansion is very small (Examples 1, 3 and 5). Meanwhile, when TFMB, PPD or m-TD is used, the transparency is high (Examples 2, 3 and 4). When these are copolymerized, the polyimide exhibits very low thermal expansibility up to a high temperature, and high transparency (Examples 6 to 10, and 12 to 16). In addition, when the polyimide film is converted into a silica-containing polyimide film, light transmittance and heat resistance are improved in the case of polyimide using DABAN (Examples 1, 20 and 21), and heat resistance is improved but the rate of linear thermal expansion is reduced in the case of polyimide using TFMB (Examples 2, 22 and 23)

As described above, the polyimide obtained from the polyimide precursor of the present invention has excellent optical transparency and bending resistance, and has a low coefficient of linear thermal expansion up to a high temperature, and therefore the polyimide film of the present invention may be suitably used as a transparent substrate for use in a display, and the like, which is colorless and transparent and on which a fine circuit can be formed.

INDUSTRIAL APPLICABILITY

According to the present invention, there may be provided a polyimide having excellent properties such as transparency, bending resistance and high heat resistance, and having a very low coefficient of linear thermal expansion; and a precursor thereof. The polyimide obtained from the polyimide precursor, and the polyimide have high transparency and a low coefficient of linear thermal expansion, which allows easy formation of a fine circuit, and have solvent resistance, and therefore the polyimides may be suitably used for the formation of a substrate for use in a display, or the like, in particular.

The invention claimed is:
1. A silica-containing polyimide, comprising:
silica particles, and
a polyimide comprising at least one repeating unit represented by the following chemical formula (5):

Chemical formula (5)

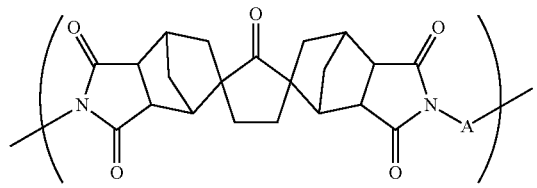

wherein A is an arylene group, and the polyimide comprises at least a repeating unit of the chemical formula (5) in which A is a group represented by the following chemical formula (3-1) or (3-2):

Chemical formula (3-1)

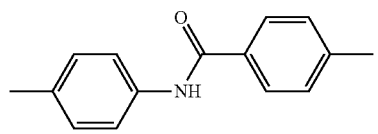

Chemical formula (3-2)

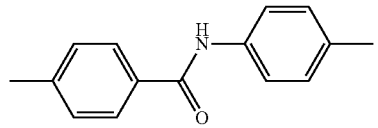

and wherein the polyimide has a coefficient of linear thermal expansion from 50° C. to 400° C. of 100 ppm/K or less, and
wherein an amount of the silica particles is 5 to 16 vol % based on the volume of the polyimide.

2. The silica-containing polyimide according to claim 1, wherein the polyimide has a light transmittance at 400 nm of 72% or more in the form of a film having a thickness of 10 μm.

3. The silica-containing polyimide according to claim 1, wherein the polyimide has a light transmittance at 400 nm of more than 75% in the form of a film having a thickness of 10 μm.

4. A substrate for a display, a touch panel or a solar battery formed from the silica-containing polyimide according to claim 1.

5. A varnish, comprising:
silica particles, and
a polyimide precursor comprising at least one repeating unit represented by the following chemical formula (1):

Chemical formula (1)

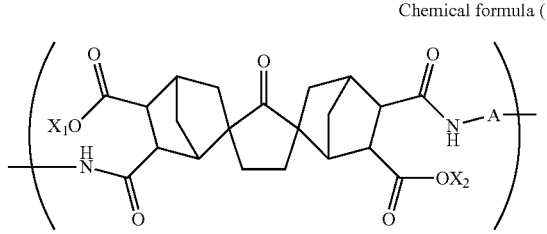

wherein A is an arylene group; and $X_1$ and $X_2$ are each independently hydrogen, an alkyl group having 1 to 6 carbon atoms, or an alkylsilyl group having 3 to 9 carbon atoms, and the polyimide comprises at least a repeating unit of the chemical formula (1) in which A is a group represented by the following chemical formula (3-1) or (3-2):

Chemical formula (3-1)

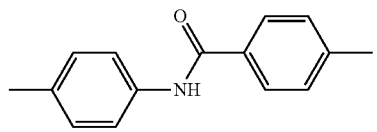

Chemical formula (3-2)

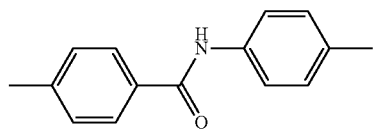

wherein a polyimide obtained from the polyimide precursor has a coefficient of linear thermal expansion from 50° C. to 400° C. of 100 ppm/K or less, and
wherein an amount of the silica particles is 5 to 16 vol % based on a volume of polyimide obtainable from the polyimide precursor.

6. A silica-containing polyimide film obtained using the varnish according to claim 5.

7. A varnish, comprising:
silica particles; and
a polyimide comprising at least one repeating unit represented by the following chemical formula (5):

Chemical formula (5)

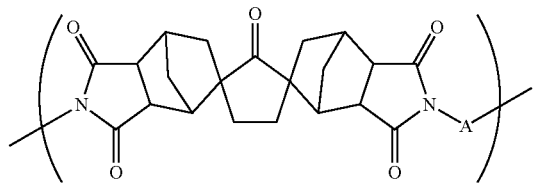

wherein A is an arylene group, and the polyimide comprises at least a repeating unit of the chemical formula (5) in which A is a group represented by the following chemical formula (3-1) or (3-2):

Chemical formula (3-1)

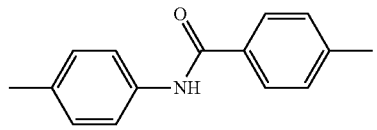

Chemical formula (3-2)

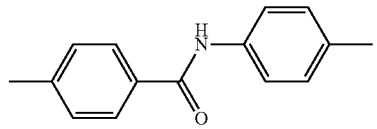

and wherein the polyimide has a coefficient of linear thermal expansion from 50° C. to 400° C. of 100 ppm/K or less, and
wherein an amount of the silica particles is 5 to 16 vol % based on a volume of the polyimide.

8. A silica-containing polyimide film obtained using the varnish according to claim 7.

* * * * *